US006379667B1

(12) United States Patent
Khaw et al.

(10) Patent No.: US 6,379,667 B1
(45) Date of Patent: Apr. 30, 2002

(54) MEDICAL USE OF MATRIX METALLOPROTEINASE INHIBITORS FOR INHIBITING TISSUE CONTRACTION

(75) Inventors: Peng Tee Khaw, London (GB); Gregory S. Schultz, Gainesville, FL (US)

(73) Assignees: University of Florida Research Foundation, Gainesville, FL (US); Moorfields Eye Hospital National Health Service Trust, London (GB)

( * ) Notice: Subject to any disclaimer, the term of this patent is extended or adjusted under 35 U.S.C. 154(b) by 0 days.

(21) Appl. No.: 09/368,307

(22) Filed: Aug. 3, 1999

Related U.S. Application Data

(62) Division of application No. 08/716,155, filed on Nov. 19, 1996, now Pat. No. 6,093,398.

(30) Foreign Application Priority Data

Mar. 16, 1994 (GB) ............................................. 9405076

(51) Int. Cl.[7] ........................ A61K 39/395; A61K 13/19
(52) U.S. Cl. ............................... 424/146.1; 424/141.1; 514/575
(58) Field of Search ................................ 514/563, 542, 514/575, 323, 419, 562; 424/146.1, 141.1

(56) References Cited

U.S. PATENT DOCUMENTS 5,189,178 A * 2/1993 Galardy et al. ............. 548/495
5,525,629 A * 6/1996 Crimmin et al. ............ 514/542

OTHER PUBLICATIONS

Grinnell, F. et al., "Collagenas–1 Complexes with α2–Macroglobulin in the Acute and Chronic Wound Environments," (1998) *J. Investigate Dermatology* 110(5):771–776.
Young, P.K. and Grinnell, "Metalloproteinase Activation Cascade After Burn Injury: A Longitudinal Analysis of the Human Wound Environment," (1994) *J. Investigative Dermatology* 103(5):660–664.
Stricklin, G.P. et al., "Localization of mRNAs representing collagenase and TIMP in sectons of healing human burn wounds," (1993) *Am. J. Pathology* 143(6):1657–1666.
Ratzenhofer et al., "Zeitschrift für Hautkrankheiten" (1978) *Z. Hautkr.* 53:929–934.
Krieg et al., "Hereditäre bullöse Epidermolysen," (1986) *Hautarzt.*, 37(4):185–189 SCRIP No. 1777, Dec. 8, 1992, p. 12.
Krieg, T. et al., "Hereditary epidermolysis bullosa, recent aspects relating to diagnosis and treatment," (1986) *Der Haurtarzt* 37:185–189 (translation from German).
Ratzenhofer, E. et al., "*In vitro* inhibition of collagenase activity in epidermolysis bullosa hereditaria dystrophica," (1978) *Zeitschrift für Hautkrankheiten* 24(53):929–934 (translation from German).

* cited by examiner

*Primary Examiner*—Nashaat T. Nashed
(74) *Attorney, Agent, or Firm*—Greenlee, Winner and Sullivan, P.C.

(57) ABSTRACT

The use of an MMP inhibitor, especially a collagenase inhibitor, in the manufacture of a medicament for the treatment of a natural or artificial tissue comprising extracellular matrix components to inhibit contraction of the tissue and methods for the treatment of tissue comprising extracellular matrix components to inhibit contraction.

14 Claims, 12 Drawing Sheets

MEDICAL USE OF MATRIX METALLOPROTEINASE INHIBITORS FOR INHIBITING TISSUE CONTRACTION

RELATEDNESS OF THE INVENTION

This application is a divisional of U.S. application Ser. No. 08/716,155 filed Nov. 19, 1996, now U.S. Pat. No. 6,093,398 which is a national stage application of PCT/GB95/00576, filed Mar. 16, 1995, claiming priority based on GB 9405076.2 filed on Mar. 16, 1994, all of which are incorporated herein in their entirety by reference to the extent not incompatible herewith.

The present invention relates to matrix metalloproteinase (MMP) inhibitors, especially collagenase inhibitors, and to their use in the manufacture of medicaments.

There are many different types of collagen found in the body and they, together with other extracellular matrix components, for example, elastin, gelatin, proteoglycan and fibronectin, make up a large proportion of the body's extracellular tissue. Matrix metalloproteinases (MMPs) are enzymes that are involved in the degradation and denaturation of extracellular matrix components. Collagenases, for example, are matrix metalloproteinases that degrade or denature collagen.

A large number of different collagenases are known to exist. These include interstitial collagenases, type IV-specific collagenases and collagenolytic proteinases. Collagenases are generally specific for collagens which, in their full triple helix structure, are extremely resistant to other enzymes.

Other MMPs are involved in the degradation and denaturing of different extracellular matrix components, for example, elastin, gelatin and proteoglycan. Some MMPs are able to degrade or denature several different types of collagen and also other extracellular matrix components. For example, stromelysin degrades type IV collagen, which is found in basement membrane, and also has an effect on other extracellular matrix components such as elastin, fibronectin and cartilage proteoglycans.

There is a classification system for MMPs, see Nagase et al 1992. For example, MMP1 is a collagenase that is sometimes called "collagenase", MMP2 is a 72kD gelatinase, MMP3 is stromelysin and MMP9 is a 92kD gelatinase. The official designations are used herein.

Collagenases have been implicated in a number of diseases, for example, rheumatoid arthritis [Mullins, D. E. et al 1983], periodontal disease and epidermolysis bullosa, and it has been proposed to use MMP inhibitors in the treatment of such conditions.

U.S. Pat. No. 5,183,900, U.S. Pat. No. 5,189,178 and U.S. Pat. No. 5,114,953 describe the synthesis of N-[2(R)-2-(hydroxamidocarbonylmethyl)-4-methylpentanoyl]-L-tryptophan methylamide, also known as GM6001, Galardin or Galardin-MPI (trade names), and other MMP inhibitors, and their use in the prevention and treatment of corneal ulceration. Treatment of corneal ulcers with peptide hydroxamic acid inhibitors has been found to assist in the healing of those ulcers. Further details of such uses are given in Schultz et al 1992.

Also described in the above-mentioned U.S. patent specifications is the use of collagenase inhibitors in situations where bacterial enzymes may be detrimental to tissue, for example, in bacterial ulceration.

Other collagenase inhibitors based on hydroxamic acid are disclosed in WO 90/05716, WO 90/05719 and WO 92/13831. Such collagenase inhibitors are disclosed as being used in the management of disease involving tissue degradation, particularly disease involving collagen breakdown, and/or the promotion of wound healing.

Other synthetic MMP inhibitors and, in particular collagenase inhibitors that have been developed include those described in EP-A-126,974 and EP-A-159,396 and in U.S. Pat. Nos. 4,599,361 and 4,743,587.

One inhibitor undergoing clinical trials is BB-94 also known as Batimastat (British Bio-technology Ltd.). Potential uses of BB-94 for the control of cancer metastasis are described in EP-A-276436. It has been proposed to use an oral formulation of BB-94 in the treatment of bone cancer.

The present invention is concerned with the contraction of tissues, for example, scars. Contraction of tissues comprising extracellular matrix components, especially of collagen-comprising tissues, may occur in connection with many different pathological conditions and with surgical or cosmetic procedures. Contracture, for example, of scars, may cause physical problems, which may lead to the need for medical treatment, or it may cause problems of a purely cosmetic nature.

It has been proposed that contraction is cell-mediated and a number of studies have suggested possible mechanisms for cell mediated collagen contraction [Gabbiani et al. 1972, Ehrlich & Rajaratnam 1990]. Investigations have been made into the role, if any, played by MMPs in the process of contracture. However, according to one proposition, MMPs are not produced during contraction [Schor et al. 1980]. According to another proposition, MMPs are produced during lattice contraction but are not implicated in the contractile process [Nakagawa et al. 1989, Mauch et al. 1989, Lambert 1992]. Instead, it has been proposed that contraction is dependent upon the extracellular lattice cell number, upon there being an intact actin cytoskeleton, and upon attachment of the cells to the extracellular matrix.

The present invention is based on the surprising observation that, during experiments on in vitro models of scar contraction, collagen (the main component of scar tissue) appears to be invaded and permanently remodelled by fibroblasts and that such invasion and remodelling is inhibited by collagenase inhibitors. The remodelling generally appears as contraction of the collagen, which contraction is inhibited by inhibition of collagenase. Furthermore, inhibition of other MMPs also results in inhibition of contraction. The observation that contraction of the tissue involves MMPs is particularly surprising since previous investigations have shown that MMPs are not produced during contraction while other investigations have indicated that MMPs are produced but are not involved in the contractile process (see above).

The present invention provides the use of an MMP inhibitor in the manufacture of a medicament for the treatment or prophylaxis of a natural or artificial tissue comprising extracellular matrix components to inhibit, i.e. restrict, hinder or prevent, contraction of the tissue, especially contraction resulting from a pathological condition or from surgical or cosmetic treatment.

The present invention also provides a method for the inhibition in vivo or in vitro of contraction of a natural or artificial tissue comprising extracellular matrix components, which comprises administering an MMP inhibitor to the tissue during and/or after its formation. Under in vivo condictions, a therapeutically effective amount of the MMP inhibitor should be administered.

The present invention especially provides the use of a collagenase inhibitor in the manufacture of a medicament for the treatment or prophylaxis of tissue comprising collagen to inhibit contraction of the tissue resulting from contraction of the collagen.

Further the present invention especially provides a method for the inhibition of contraction of tissue comprising collagen, resulting from contraction of the collagen, which comprises administering a therapeutically effective amount of a collagenase inhibitor to the tissue.

The methods of the present invention may be used for medical or cosmetic treatment.

The invention provides a method for the inhibition, for cosmetic reasons, of disfigurement caused by contraction of tissue comprising extracellular matrix components, which method comprises administering a matrix metalloproteinase inhibitor to the tissue.

Cosmetic treatments, such as chemical or physical dermal abrasion, used as anti-ageing treatments, cause trauma to the skin. Use of MMP inhibitors during the healing process which occurs after the initial abrasion is a cosmetic use of MMP inhibitors according to the present invention.

The present invention also provides the use of an MMP inhibitor to inhibit, i.e. restrict, hinder or prevent, invasion by cells, especially fibroblasts, into tissue comprising an extracellular matrix and/or migration by cells, especially fibroblasts, in or through tissue comprising an extracellular matrix.

The term "MMP inhibitor" is used herein to denote any substance that is capable of inhibiting, i.e. restricting, hindering or preventing, the action of an MMP. The term "collagenase inhibitor" is used herein to denote any substance that is capable of inhibiting, i.e. restricting, hindering or preventing, the action of a collagenase. A collagenase inhibitor may be specific for one particular collagenase or may inhibit several different collagenases. A collagenase inhibitor may also inhibit other MMPs, in which case it may also be defined as an MMP inhibitor.

The term "inhibitor" as used herein includes agents that act indirectly by inhibiting the production of the relevant enzyme, for example an antisense molecule, as well as agents that act directly by inhibiting the enzyme activity of the relevant enzyme, such as, for example, a conventional inhibitor.

An MMP, e.g. collagenase, inhibitor may be naturally-occurring or synthetic. An MMP, e.g. collagenase, inhibitor may be an anti-MMP, e.g. anti-collagenase, antibody, either polyclonal or monoclonal. The inhibitory activity of a putative MMP inhibitor may be assessed by any method suitable for determining inhibitory activity of a compound with respect to an enzyme. Such methods are described in standard textbooks of biochemistry. A more detailed description of MMP, e.g. collagenase, inhibitors is given below.

Collagen is the major component of scar and other contracted tissue and as such is the most important structural component to consider. Nevertheless, scar and other contracted tissue also comprises other structural components, especially other extracellular matrix components, for example, elastin, which may also contribute to contraction of the tissue. MMPs are involved in the synthesis and degradation of such components. In general, a collagenase inhibitor is used as the MMP inhibitor in accordance with the present invention but, it may be appropriate to use instead an inhibitor of an MMP other than a collagenase. It may be particularly advantageous to use a combination of a collagenase inhibitor and one or more inhibitors of other MPs or to use an inhibitor which inhibits both a collagenase and at least one or more other MMPs.

The mechanism and control of contraction of tissues comprising extracellular matrix components, for example, collagen-comprising tissues, is still poorly understood. Some degree of contraction appears to be part of the healing process, but the trigger for contraction is not known. The involvement of MMPs in contraction of tissues, for example, scar tissue, and the utility of MMP inhibitors according to the present invention in the inhibition, i.e. prevention, restriction and hindering, of contraction has been confirmed by the following experimental data:

When fibroblasts in an in vitro collagen gel model of scar contraction are subjected to antiproliferative agents after contraction has occurred, there is no significant expansion of the collagen gel, that is to say, no relaxation of the contraction, even when the fibroblast cells have been killed and the supporting cytoskeleton of the cells removed. The remodelling of collagen leading to contraction therefore appears to result from activity of one or more enzymic systems of the fibroblasts.

Fibroblasts involved in the contraction of collagen produce greater amounts of matrix metalloproteinase mRNAs and proteins than do control fibroblasts. This is associated with cellular invasion of the collagen. Invasion of the collagen and contraction are inhibited by the use of inhibitors specific to those MMPs coded for by the mRNAs which are present at higher levels in cells involved in contraction than in control cells:

Quantitative competitive reverse transcriptase polymerase chain reaction (QCRT-PCR) technique [Tarnuzzer & Schultz 1994] was used to study the levels of MMP mRNA produced by human ocular fibroblasts in collagen Type I lattices undergoing contraction in comparison with human ocular fibroblasts in monolayer cultures. It was found that in the collagen lattices the fibroblasts produced more mRNA for collagenase (MMP1), 72 kD gelatinase (MMP2) and stromelysin (MMP3) but not for 92 kD gelatinase (MMP9) than did the control cells in the monolayer culture. Levels of mRNA for MMPs 1, 2 and 3 in the lattices were found to be greater than those in the monolayer cultures; over 100 times greater at certain times during the contraction process (see Example 4 below). Gelatin zymography [Heussen & Dowdle 1980] was used to analyse and compare production of the gelatinolytic components of the cells. It was found that gelatinolytic activity was increased compared to controls. It appeared, therefore, that the increased mRNA production resulted in increased protein production.

Antibodies against MMPs 1, 2, 3 and 9 were tested as contraction inhibitors. It was found that the antibodies against MMPs 1, 2 and 3 gave significant inhibition of the contraction of collagen gels by human ocular fibroblasts but that the antibody against MMP9 did not result in inhibition of contraction.

In the present specification the term "contraction of collagen" includes not only shrinkage of collagen but also any remodelling of collagen that leads to contraction of the tissue comprising that collagen. It also includes contributions made by other components of the tissue, especially other extracellular matrix components, for example, elastin.

As indicated above, contraction of tissues comprising extracellular matrix components, especially of collagen-comprising tissues, may occur in connection with many different pathological conditions and with surgical or cosmetic procedures. Contracture may cause physical problems, which may lead to the need for medical treatment, or it may cause problems of a purely cosmetic nature. It is therefore very valuable to have medicaments capable of inhibiting, i.e. restricting, hindering or preventing, such contraction. Important uses of such medicaments are described below. It should be understood, however, that the uses according to the present invention are not restricted to the manufacture of medicaments, or to methods of treatment, medical or cosmetic, suitable for the conditions described below. The present invention also includes use in the manufacture of medicaments or in methods of treatment suitable for use in any case where contraction of tissue comprising extracellular matrix components resulting substantially from extracellular matrix component contraction is occurring or may occur.

Although the discussion below refers specifically to collagen contraction and the use of collagenase inhibitors, broad spectrum MMP inhibitors and/or inhibitors of MMPs other than collagenases may be used in inhibiting contraction of tissue comprising extra-cellular matrix components and the present invention is to be understood as including the use of such MMP inhibitors as an alternative to the use of collagenase-specific inhibitors in the treatment of tissue comprising extracellular matrix components. The present invention also includes the use of broad spectrum MMP inhibitors and/or inhibitors of MMPs other than collagenases in addition to the use of collagenase inhibitors, for example, in the treatment of tissue comprising extracellular components especially collagen comprising-tissue.

Contraction of collagen-comprising tissue, which may also comprise other extracellular matrix components, frequently occurs in the healing of burns. The burns may be chemical, thermal or radiation burns and may be of the eye, the surface of the skin or the skin and the underlying tissues. It may also be the case that there are burns on internal tissues, for example, caused by radiation treatment. Contraction of burnt tissues is often a problem and may lead to physical and/or cosmetic problems, for example, loss of movement and/or disfigurement. The present invention therefore includes the use of MMP inhibitors, for example, collagenase inhibitors, for example, in the form of a medicament, to inhibit contraction of the burnt tissue as it heals.

A further aspect of the present invention is the inhibition of the contraction of skin grafts. Skin grafts may be applied for a variety of reasons and may often undergo contraction after application. As with the healing of burnt tissues the contraction may lead to both physical and cosmetic problems. It is a particularly serious problem where many skin grafts are needed as, for example, in a serious burns case.

An associated area in which the medicaments and methods of the present invention are of great use is in the production of artificial skin. To make a true artificial skin it is necessary to have an epidermis made of epithelial cells (keratinocytes) and a dermis made of collagen populated with fibroblasts. It is important to have both types of cells because they signal and stimulate each other using growth factors. A major problem up until now has been that the collagen component of the artificial skin often contracts to less than one tenth of its original area when populated by fibroblasts. MMP inhibitors, for example, collagenase inhibitors,may be used to inhibit the contraction to such an extent that the artificial skin can be maintained at a practical size.

One area of particular interest is the use of MMP, e.g. collagenase,inhibitors to prevent or reduce contracture of scar tissue resulting from eye surgery. Glaucoma surgery to create new drainage channels often fails due to scarring and contraction of tissues. A method of preventing contraction of scar tissue formed in the eye, such as the application of a suitable agent, is therefore invaluable. Such an agent may also be used in the control of the contraction of scar tissue formed after corneal trauma or corneal surgery, for example laser or surgical treatment for myopia or refractive error in which contraction of tissues may lead to inaccurate results. It is also useful in cases where scar tissue is formed on/in the vitreous humor or the retina, for example, that which eventually causes blindness in some diabetics and that which is formed after detachment surgery, called proliferative vitreoretinopathy. Other uses include where scar tissue is formed in the orbit or on eye and eyelid muscles after squint, orbital or eyelid surgery, or thyroid eye disease and where scarring of the conjunctiva occurs as may happen after glaucoma surgery or in cicatricial disease, inflammatory disease, for example, pemphigoid, or infective disease, for example, trachoma. A further eye problem associated with the contraction of collagen-comprising tissues for which the methods and medicaments of the present invention may be used is the opacification and contracture of the lens capsule after cataract extraction.

Cicatricial contraction, contraction due to shrinkage of the fibrous tissue of a scar, is common. In some cases the scar may become a vicious cicatrix, a scar in which the contraction causes serious deformity. A patient's stomach may be effectively separated into two separate chambers in an hour-glass contracture by the contraction of scar tissue formed when a stomach ulcer heals. Obstruction of passages and ducts, cicatricial stenosis, may occur due to the contraction of scar tissue. Contraction of blood vessels may be due to primary obstruction or surgical trauma, for example, after surgery or angioplasty. Stenosis of other hollow visci, for examples, ureters, may also occur. Problems may occur where any form of scarring takes place, whether resulting from accidental wounds or from surgery. Medicaments comprising MMP inhibitors, e.g. collagenase inhibitors, may be used wherever scar tissue is likely to be formed, is being formed or has been formed.

Conditions of the skin and tendons which involve contraction of callagen-comprising tissues include post-trauma conditions resulting from surgery or accidents, for example, hand or foot tendon injuries, post-graft conditions and pathological conditions, such as scleroderma, Dupuytren's contracture and epidermolysis bullosa. Scarring and contraction of tissues in the eye may occur in various conditions, for example, the sequelae of retinal detachment or diabetic eye disease (as mentioned above). Contraction of the sockets found in the skull for the eyeballs and associated structures, including extra ocular muscles and eyelids, may occur if there is trauma or inflammatory damage. The tissues contract within the sockets causing a variety of problems including double vision and an unsightly appearance.

Although the above discussion relates in particular to humans, animals may exhibit the conditions described above or similar or analogous conditions. The present invention therefore also relates analogously to medicaments and methods for use in veterinary practice for the treatment and care of animals and especialy for use in the treatment and care of mammals.

The present invention provides a method of treating a human or other mammal to inhibit contraction of tissue comprising an extracellular matrix component, especially contraction associated with a chemical burn, a thermal burn or a radiation burn, a skin graft, a post-trauma condition resulting from surgery or an accident, glaucoma surgery, diabetes associated eye disease, scleroderma, Dupytren's contracture, epidermolysis bullosa or a hand or foot tendon injury, which comprises administering to the human or other mammal a therapeutically effective amount of an MMP inhibitor.

It appears that MMP inhibitors, e.g. collagenase inhibitors, inhibit contraction tissues comprising extracellular components, for example, collagen, caused by cells such as fibroblasts but do not appear to be able to bring about significant reversal of such contraction. Accordingly, tissue which is being affected should generally be treated at the time when the contraction is occurring. Preferably treatment should take place as early as possible, advantageously as soon as, and most advantageously before, the first signs of contraction are observed. In treatments, conditions or healing processes where contraction of extracellular component, e.g. collagen, comprising tissue is common. MMP inhibitors, e.g. collagenase inhibitors, may be used as a routine prophylactic measure before any signs of contraction have actually been seen.

Since active contraction appears to be associated with active production of MMPs, the treatment used to prevent the contraction should be continued over at least the period during which contraction is likely to occur. This may often be quite a significant period of time, for example, several years or even longer. Contraction may still occur even after an initially open wound appears to have healed, for example, in patients with burns. Also conditions such as hand tendon contraction involve contraction even though there is no wound as such.

As indicated above, the present invention involves the use of MMP inhibitors, especially collagenase inhibitors.

Both natural and synthetic MMP inhibitors (inhibitors of enzyme activity), including collagenase inhibitors, are known. Naturally-occurring MMP inhibitors include $\alpha_2$-macroglobulin, which is the major collagenase inhibitor found in human blood [Eisen et al 1970]. Naturally occurring MMP inhibitors are also found in tissues. The presence of tissue inhibitors of MMPs has been observed in a variety of explants and in monolayer cultures of mammalian connective tissue cells [Vater et el 1979 and Stricklin and Wegus 1983]. Not only collagenase inhibitors but also inhibitors for other MMPs, for example, gelatinase and proteoglycanase are found. MMP inhibitors are generally unable to bind the inactive (zymogen) forms of the respective enzymes but complex readily with active forms [Murphy et al 1981]. Tissue MMP inhibitors are found, for example, in dermal fibroblasts, human lung, gingival, tendon and corneal fibroblasts, human osteoblasts, uterine smooth muscle cells, alveolar macrophages, amniotic fluid, plasma, serum and the $\alpha$-granule of human platelets [Stricklin and Wegus 1983; Welgus et al 1985; Welgus and Stricklin 1983; Bar-Sharvit et al 1985; Wooley et al; 1976; and Cooper et al 1985].

Synthetic collagenase inhibitors and inhibitors for other MMPs have been and are being developed. Compounds such as EDTA, cysteine, tetracycline and ascorbate are all inhibitors of collagenases but are relatively non-specific. As indicated above, synthetic inhibitors that have defined specificity for MMPs, including collagenase inhibitors, are described in the literature. For example, U.S. Pat. Nos. 5,183,900, 5,189,178 and 5,114,953 describe the synthesis of N-[2(R)-2-(hydroxamidocarbonylmethyl)-4-methylpentanoyl]-L-tryptophan methylamide, also known as GM6001 or Galardin (trade name), and other MMP inhibitors. Other collagenase inhibitors based on hydroxamic acid are disclosed in WO 90/05716, WO 90/05719 and WO 92/13831. Further synthetic MMP inhibitors and in particular collagenase inhibitors that have been developed include those described in EP-A-126,974 and EP-A-159,396 and in U.S. Pat. Nos. 4,599,361 and 4,743,587.

Yet another inhibitor is BB-94, also known as Batimastat (British Bio-technology Ltd.), see for example, EP-A-276436. Disclosed in WO90/05719 as having particularly strong collagenase inhibiting properties are (4-(N-hydroxyamino)-2R-isobutyl-3S-(thio-phenyl-thiomethyl)succinyl]-L-phenylalanine-N-methylamide (especially good) and [4-(N-hydroxyamino)-2R-isobutyl-3S-(thiomethyl)succinyl]-L-phenylalanine-N-methylamide and in WO90/05716 [4-(N-hydroxyamino)-2R-isobutylsuccinyl]-L-phenylalanine-N-(3-aminomethylpyridine) amide and [4-N-hydroxyamino)-2R-isobutyl-3S-methylsuccinyl]-L-phenylalanine-N-[4-(2-aminoethyl)-morpholino] amide.

The contents of the patent specifications and literature references mentioned herein are hereby incorporated by reference.

As indicated above, the properties of natural and synthetic collagen inhibitors may vary. Individual inhibitors often have different specificities and potencies. Some inhibitors are reversible, others are irreversible. In general the more potent an inhibitor's inhibitory effects on a collagenase the better. For some uses an inhibitor specific to one particular collagenase may be required but generally a broad spectrum MMP inhibitor, for example, GM6001 (Galardin (trade name)), is preferred.

GM6001 (Galardin (trade name)) is a very potent MMP inhibitor that is effective against collagenase. It has the structure:

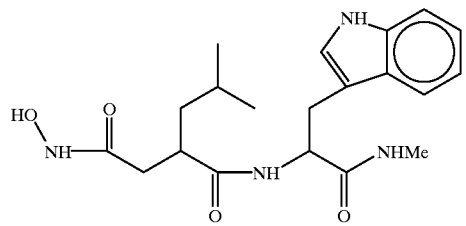

A detailed account of its ability to inhibit human skin fibroblast collagenase, thermolysin and *Pseudomonas aeruginosa* elastase is given in Grobelny et al, 1992. Its inhibition constants with three types of MMPs are now calculated to be:

| | |
|---|---|
| collagenase | Ki = 0.4 nmol/1 |
| gelatinase | Ki = 0.4 nmol/1 |
| stromelysin | Ki = 20 nmol/1 |

Preferred MMP inhibitors for use according to the present invention include GM6001 (Galardin) and those synthetic inhibitors described and referred to above. Preferred inhibitors include peptide hydroxamic acids or pharmaceutically acceptable derivatives thereof. Especially preferred are those compounds that are described and claimed in U.S. Pat. No. 5,189,178; U.S. Pat. No. 5,183,900 or U.S. Pat. No. 5,114,953 and that are collagenase inhibitors. Those with low Ki values, i.e. high pKi values are generally preferred. GM6001 (Galardin (trade name)) is an MMP inhibitor that is especially preferred because it is one of the most potent collagenase inhibitors known at present. However, for certain applications it may be preferable to use a less potent (weaker) inhibitor.

The preferred broad spectrum MMP inhibitor for use in accordance with the present invention is GM6001 (Galardin (trade name)). It is able to inhibit the action not only of collagenases but of other MMPs as well.

Also preferred are inhibitors that are capable of inhibiting MMPs 1, 2 and 3 (collagenase, 72 kD gelatinase and stromelysin, respectively). These may be used individually or in combination.

As indicated above, an anti-MMP polyclonal or monoclonal antibody, especially an anti-collagenase antibody, may be used as an inhibitor. An MMP antigen may be used in immunisation protocols to obtain polyclonal antisera immunospecific for that enzyme. The antigen may be a hapten derived from an MMP, especially from an active site region, or may be a full-length MMP or a fragment thereof. Using standard protocols and mammalian subjects, such as rabbits or mice, polyclonal antibodies may be obtained. Those may then be used as inhibitors. Monoclonal antibodies may be produced according to standard procedures, for example, using an appropriate MMP antigen, for example, a collagenase antigen.

Antibodies which are specific for a particular MMP may be made and the use of such specific inhibitors may be preferred under certain circumstances. For example, an antibody to MMP1, MMP2 or MMP3 (collagenase, 72 kD gelatinase or stromelysin respectively) or a mixture of two or more thereof may be used.

An alternative method of inhibiting the action of an MMP is to reduce the amount of the MMP by preventing its production. One method of preventing protein production is by the use of antisense nucleic acid molecules. An antisense molecule need not be large; 20 base pairs is often sufficient. If the molecule is small it should be able to enter the cells unaided but liposomes can be used to assist entry if required. An antisense molecule will usually be designed to attach to the MMP mRNA but may be designed to attach to the appropriate DNA during replication and transcription.

Although antibodies usually bind to proteins it is possible to produce antibodies which bind to nucleic acids. Accordingly, there may be used as an inhibitor according to the present invention an antibody that binds to the mRNA or the DNA of the selected MMP and hence hinders production of the MMP.

Reducing the production of an MMP has the advantage that it should be possible to use a smaller amount of inhibitor than is required for direct inhibition of MMP enzyme activity because each MMP mRNA molecule and the MMP DNA is responsible for the production of many MMP enzyme molecules.

Inhibitors for use according to the present invention must be able to be used in high enough concentrations and large enough doses to give adequate inhibition without being toxic to cells with which they come into contact.

For the treatment of some conditions it may be preferred to use a medicament containing a collagenase inhibitor and at least one other enzyme inhibitor. That additional inhibitor may also have collagenase inhibitory properties and/or it may have inhibitory properties for a different enzyme, for example, for a different MMP. If two or more inhibitors are used then the second and any additional inhibitor preferably has inhibitory properties for an enzyme other than a collagenase. Additional inhibitors may be, for example, inhibitors of other MMPs such as a gelatinase or a stromelysin, or inhibitors of other enzymes that break down tissue such as serine proteases, for example, a serine protease inhibitor such as aprotinin may be used.

Cytokines, for example, interleukin-1, in the environment of collagen-comprising tissue may stimulate collagenase production and so it may also be preferable to include an inhibitor of cytokines in the manufacture of medicaments or in methods of treatment according to the present invention.

Medicaments according to the present invention are generally provided in a pharmaceutical preparation form suitable for topical administration, for example, an emulsion, suspension, cream, lotion, ointment, drops, foam or gel. Such preparations are generally conventional formulations, for example, as described in standard text books of pharmaceutics such as the British Pharmacopoeia. Other suitable pharmaceutical forms for topical administration include dry powders, aerosols and sprays, which may be especially suitable for application to burns. Further suitable pharmaceutical preparation forms include those for administration by injection or infusion, for example, sterile parenteral solutions or suspensions, especially for administration directly into, or into the area of, the extracellular matrix component, e.g. collagen, comprising tissue, for example, by subconjunctival, subcutaneous, interpleural or intraperitoneal injection, and also slow release delivery systems, for example, liposome systems.

The invention especially provides a pharmaceutical preparation, (other than a preparation suitable for use in the eye), suitable for application to a wound, including an ulcer, a burn or skin graft comprising a matrix metalloproteinase inhibitor. Advantageously the preparation is in the form of a solution, suspension, cream, ointment, or gel, in which the MMP inhibitor is in a concentration of from 0.4 $\mu$g/ml to 400 $\mu$g/ml. The MMP inhibitor is preferably a collagenase inhibitor.

Oral formulations may also be used. These may be in the form of tablets, capsules, powders, granules, lozenges or liquid or gel preparations. Tablets may be coated by methods well known in normal pharmaceutical practice. Liquid formulations include syrups. Oral formulations may be used to treat directly conditions such as stomach ulcers and may also be used to treat conditions systemically.

The inhibitor(s) may be dissolved or dispersed in a diluent or carrier. The choice of carrier depends on the nature of the inhibitor, its solubility and other physical properties, and on the method and site of application. For example, only certain carriers are suitable for preparations for use in the eye.

Carriers include ethylene glycol, silver sulphadiazine cream and hypromellose. These may be used in creams and drops. An acetate buffer system may also be used. Further pharmaceutically suitable materials that may be incorporated in pharmaceutical preparations include absorption enhancers, pH regulators and buffers, osmolarity adjusters, emollients, dispersing agents, wetting agents, surfactants, thickeners, opacifiers, preservatives, stabilizers and antioxidants, foaming agents and flocculants, lubricants, colourants and fragrances (generally only in primarily cosmetic preparations).

Gels and liposomes may be the preferred delivery method when the inhibitor is an antisense molecule.

Preferably a medicament according to the present invention is applied directly to an open wound or is injected directly into the site of tissue contraction.

Suitable medicaments may, however, be applied to the skin surface where the tissue to be treated is below that surface, the active ingredient then being absorbed by and passing through the skin. Penetration enhancers are preferably incorporated in such medicaments.

Medicaments according to the present invention comprising MMP inhibitors, for example, collagenase inhibitors, for use in the inhibition of the contraction of tissues comprising extracellular matrix components, for example, collagen-comprising tissues, may contain further pharmaceutically active ingredients, for example antibiotics, antifungals, steroids, and further enzyme inhibitors, for example, serine protease inhibitors (as described above). Further components for certain indications include growth or healing promoters such as epidermal growth factor (EGF), fibronectin and aprotinin. As mentioned above cytokine inhibitors may also be included.

The inhibitors will generally be used in liquid and other non-solid formulations having concentrations of around 0.4 to 400 $\mu$g/ml. In some cases, however, higher concentrations may be required. The total amount used and the dose administered will depend on the severity and area of the contraction, the condition causing it and the physical characteristics of the patient and the site and method of administration.

The following non-limiting Examples illustrate the invention. The Examples relate to experiments carried out in vitro; the teachings are directly applicable in vivo, for example, to the treatment of humans and mammals, for example, as described in the specification.

The Examples illustrate the use of MMP inhibitors in vitro models of scar contraction and of artificial skin. They also include experiments which illustrate the lack of toxicity to cells of MMP inhibitors and their effect on cell morphology. Further experiments investigate the levels of some MMP mRNA and of some MMPs present in cells during contraction.

FIG. 8A shows a control gel and FIG. 8B shows a gel exposed to inhibitor.

FIG. 9A shows a control gel and FIG. 9B shows a gel exposed to inhibitor.

FIG. 10A shows a control gel and FIG. 10B shows a monolayer exposed to inhibitor.

FIG. 11A shows a control gel and FIG. 11B shows a gel exposed to inhibitor.

EXAMPLES

Example 1

Preparation of Materials (a) Collagen Solutions

Figure 1:
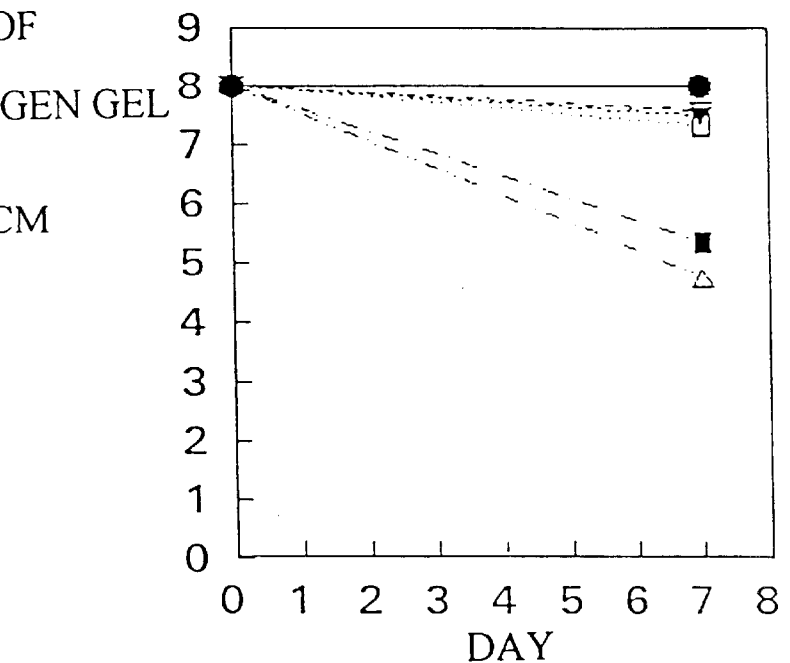
FIG. 1 is a diagrammatic representation of the results of the experiments described in Example 1. It is a graph showing the area of fibroblast populated collagen gel over time for a number of different culture regimes.

Solutions of type 1 collagen were prepared by dissolving 100 mg of collagen in 20 ml of 0.1% (v/v) glacial acetic acid in distilled water. The collagen was sigma type 1 collagen and was prepared by the method of Bornstein MB Lab Invest 7134 1958.

(b) Concentrated Culture Medium

A concentrated tissue culture medium was prepared by mixing the following:

35 ml distilled water 15 ml 10×MEM (Eagle's minimal essential medium)

1.5 ml glutamine 1.5 ml fungizone (amphotericin B 250 $\mu$g/ml of water)

1.5 ml 10,000 units penicillin/10 mg streptomycin per ml solution (solvent is water)

4 ml 7.5% (w/v) sodium bicarbonate solution Solutions of 4.9 ml of the concentrated culture medium in 180 μl of 0.1M sodium hydroxide solution were used in the preparation of collagen gels.

(c) Collagenase Inhibitor Solutions and Control Solutions

Solutions having three different concentrations of collagenase inhibitor (400, 40 and 4 μg/ml), a buffer solution (control 1) and a normal growth medium solution (control 2) were prepared as described below. The collagenase inhibitor used was GM6001 (Galardin (trade name)). 50 μl of glacial acetic acid was added to 11 mg of collagenase inhibitor and the inhibitor was allowed to dissolve. The pH of a 24.875 ml aliquot of serum-free HEPES (N-[2-hydroxyethylpiperazine-N'-[2-ethane sulfonic acid]) buffered DMEM (Dulbecco's Modified Eagle's Medium) was adjusted to pH 8 using sterile 1M sodium hydroxide solution and the aliquot was then added to the inhibitor solution. The resulting solution had an inhibitor concentration of 400 μg/ml.

The 400 μg/ml solution was serially diluted with serum-free HEPES-DMEM to give solutions containing the collagenase inhibitor at concentrations of 40 and 4 μg/ml.

The solutions of all three concentrations were then supplemented with 10% (v/v) newborn calf serum.

The buffer solution (control 1) was prepared by adding 50 μl of glacial acetic acid to a 24.875 ml aliquot of serum-free HEPES buffered DMEM of pH 8 (pH adjusted with sterile 1M sodium hydroxide solution as above), then readjusting the pH to pH 7.4 with 1M sterile sodium hydroxide solution and finally supplementing with 10% (v/v) of newborn calf serum (NCS).

The normal growth medium solution (control 2) was prepared by supplementing an aliquot of serum-free HEPES buffered DMEM with 10% (v/v) newborn calf serum.

The pH and osmolarity of the test and control solutions were measured, see Table 1, Treatment of Gels with Test Solutions.

(d) Cell Cultures

Cultures of human ocular fibroblasts were grown, in the normal way (see Khaw P. T. et al 1992 for the method of growth), until the monolayers (single layers of cells on a plastic culture disc, not embedded in a matrix) were just subconfluent. They were then removed from their substratum via a treatment with trypsin and were pelleted by centrifugation at 3000×g for 8 minutes. The supernatant was then discarded and the cell pellet resuspended in 1.1 ml of newborn calf serum. 100 μl of the suspension was removed and counted in a Coulter counter (Model ZF).

(e) Collagen Gels

Each collagen gel had a final volume of 1.1 ml made up of 0.6 ml of a solution of type 1 collagen obtained according to (a) above, 0.35 ml of concentrated culture medium prepared according to (b) above, and 0.15 ml of cell suspension containing 100,000 cells prepared as described in (d) above.

Triplicate gels were made by adding 1.05 ml of the concentrated medium to 1.8 ml of the type 1 collagen solution, mixing rapidly and then adding 0.45 ml of a cell suspension containing 300,000 cells and mixing rapidly.

1 ml aliquots of this gel were then added to petri dishes (area=8 cm$^2$) and then the dishes were rotated so that the gels were evenly distributed across the bottoms of the dishes. The gels were then incubated at 37° C. in 5% $CO_2$ in air until they had solidified (usually 3 to 5 minutes). An area of the gel was then detached from the edge of each petri dish and 3 ml of normal growth medium solution (control 2), inhibitor test solution or buffer solution (control 1), were added. Each gel was then fully detached from the edges and bottom of the petri dish so that free-floating gels were obtained.

Treatment of Gels with Test Solutions

The gels, after solidification, were treated for 24 hours with 3 ml of each of the following test solutions:

TABLE 1

| Test Solution | pH | Osmolarity |
| --- | --- | --- |
| 1) Collagenase inhibitor at 400 μg/ml | 7.8 | 421 |
| 2) Collagenase inhibitor at 40 μg/ml | 7.8 | 339 |
| 3) Collagenase inhibitor at 4 μg/ml | 7.9 | 329 |
| 4) Buffer (control 1) | 7.8 | 404 |
| 5) Normal growth medium (control 2) | 7.8 | 331 |

The test and control solutions were replaced by 3 ml of the appropriate fresh solution after 24 hours. Photographs of the gel areas were taken on days 1 and 2 and were then digitised. The resulting data were processed by a computer and the gel areas were calculated. Phase-contrast photographs were taken of the top and middle of each gel after 1 and 2 days.

Results

The changes in area observed for the collagen gels over the 2 day test period are shown in FIG. 1. (In FIG. 1 mcg represents micrograms.) It can be seen from the results that all the solutions of collagenase inhibitor inhibited the contraction of the collagen gels in comparison with the buffer solution (control 1) and the normal growth medium solution (control 2). The amount of inhibition observed was dose dependent; the solution with the highest inhibitor concentration showed the strongest inhibition of gel contraction. The buffer solution (control 1) also showed some inhibitory properties in comparison with the normal growth medium solution (control 2) but the effect was not significant when compared to that exhibited by the buffered collagenase inhibitor solution of even the lowest concentration. At the end of the tests the cells in the collagen gels were still alive and phase contrast microscopy showed that they appeared to be viable.

Discussion

It appears that MMPs are involved in fibroblast mediated contraction of collagen and that the use of an inhibitor can restrict contraction without killing the cells. Furthermore, the amount of inhibition is dose dependent.

Example 2

The toxicity of GM6001 (Galardin (trade name)) and a second collagenase inhibitor GM1489 (a derivative of GM6001) to fibroblasts was tested at various concentrations.

The toxicity of the inhibitors was tested by measuring DNA synthesis by tritiated thymidine incorporation. The assay was adapted from a procedure previously described, Woost, P. G. et al 1992.

Figure 2:
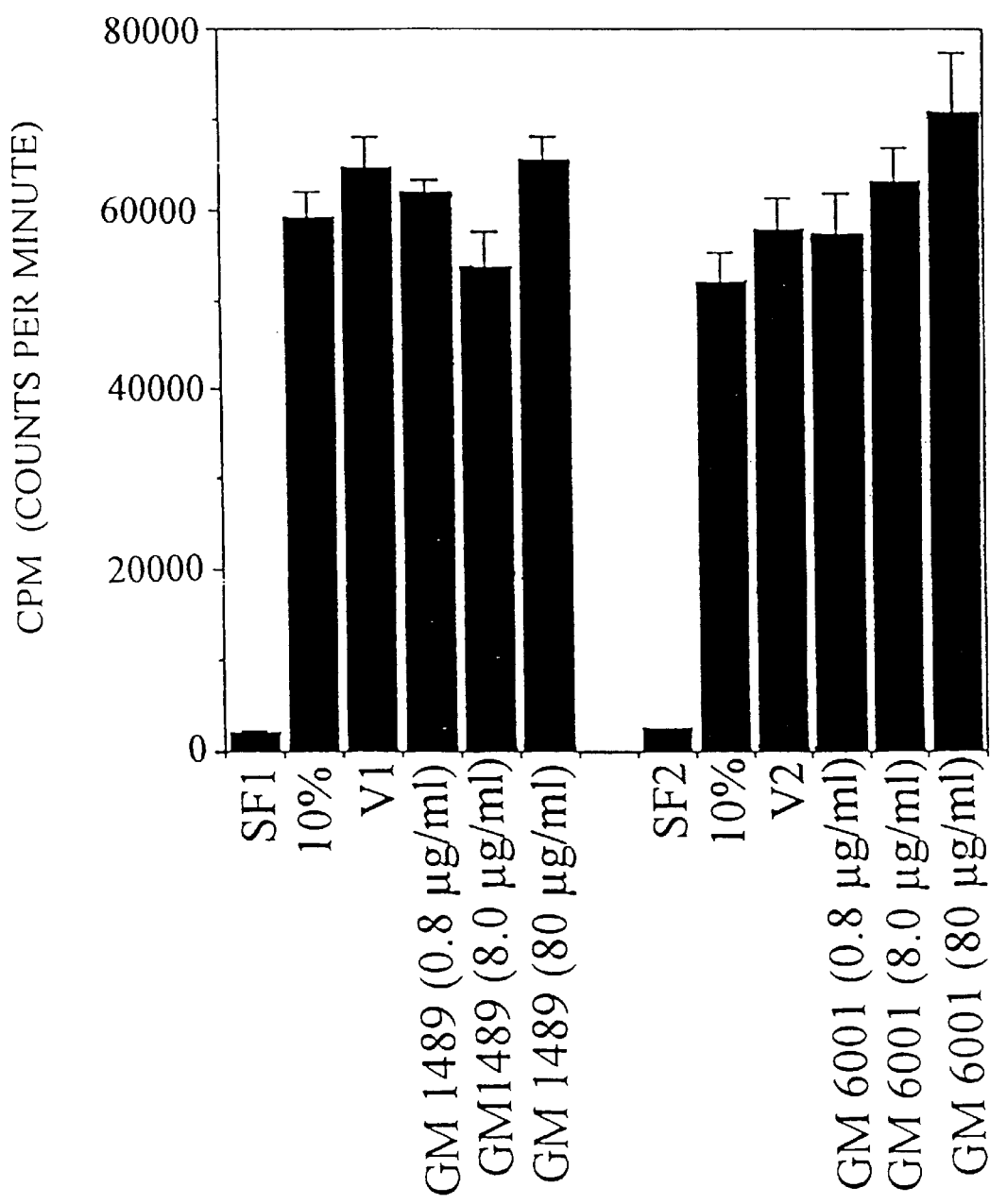
FIG. 2 is a diagrammatic representation of the results of the experiments described in Example 2. It is a histogram showing counts per minute of radiation emitted by cells grown under a number of different conditions.

Human ocular fibroblasts (Tendon's capsule fibroblasts) were cultured in Trimix (DMEM/F-10/ M-199) cell culture medium (available from GIBCO/BRL) supplemented with 10% bovine calf serum and grown to confluency in T-75 tissue culture flasks. (That is flasks having a surface area of 75 cm$^2$.) The cells were split and seeded into 24 well plates at a density of 1×10$^4$/well in 1.0 ml of medium with 10% bovine calf serum. The cells were incubated for 24–36 hours or until they reached 60–70% confluency. The medium was then changed to serum-free Trimix and the cells were incubated for an additional 24 hours. The cells were then incubated in quadruplicate wells for 24 hours with 1.0 µCi/well $^3$H-thymidine in the following conditions: serum-free medium (Trimix), medium plus 10% serum, medium plus 10% serum and vehicle, alone or with the inhibitors. The vehicle was a buffered acetate solution. The solutions comprising medium with 10% serum and vehicle, alone or with inhibitors, were prepared by the method described in Example 1, section (c), above, using Trimix instead of the HEPES buffered DMEM. The inhibitors, GM6001 and GM1489, were each tested at concentrations of 80.0, 8.0, and 0.8 µg/ml. At the end of the incubation period, the wells were washed 3 times with PBS and fixed with 12.5% TCA for 10 min followed by methanol for 10 min. The plates were air dried and the cells solubilized in 1.0 ml of 0.2 N NaOH at 37° C. for 1 hour. Radioactivity was determined by liquid scintillation counting 900 ml of the solubilized cells. The experiments show that there is no significant toxicity at any of the concentrations tested. The results are shown in FIG. 2. In FIG. 2 SF1 and SF2 stand for serum-free medium, 10% for medium plus 10% serum, V1 and V2 for medium plus 10% serum and vehicle and the other results are for the inhibitor solutions (comprising also media plus 10% serum and vehicle).

FIG. 2 shows the thymidine incorporation of the ocular fibroblasts at different concentrations of each collagenase inhibitor.

Discussion

It can be seen that there is no significant reduction in thymidine uptake even with the highest concentrations of the inhibitors. This indicates that the reduction in collagen contraction found when using collagenase inhibitors is not due to inhibition of cell proliferation.

In the following Examples methods and materials substantially as described in Example 1 are used except where it is indicated to the contrary.

Example 3

This experiment was designed to investigate the effect of the following MMP inhibitors: Galardin, BB-94 and antibodies to MMPS, 1, 2 3 and 9, on ocular fibroblast mediated collagen contraction.

The preparation of materials was as described in Example 1 above except where indicated. Test solutions were used in approximately 3 ml doses. For all contraction experiments cell morphology was monitored by phase contrast microscopy and the growth medium was changed every 3 to 4 days.
a) Cell Number Dependence Collagen gels were seeded with either 100,000 or 500,000 cells. They were exposed to inhibitor and control solutions comprising 40 µg/ml and 4 µg/ml of Galardin or equimolar hydroxamic acid (control) at an equivalent to 40 µg/ml of Galardin (100 µM) (made up as described in Example 1(c) above). The gels were monitored for 7 days.

Figure 3A:
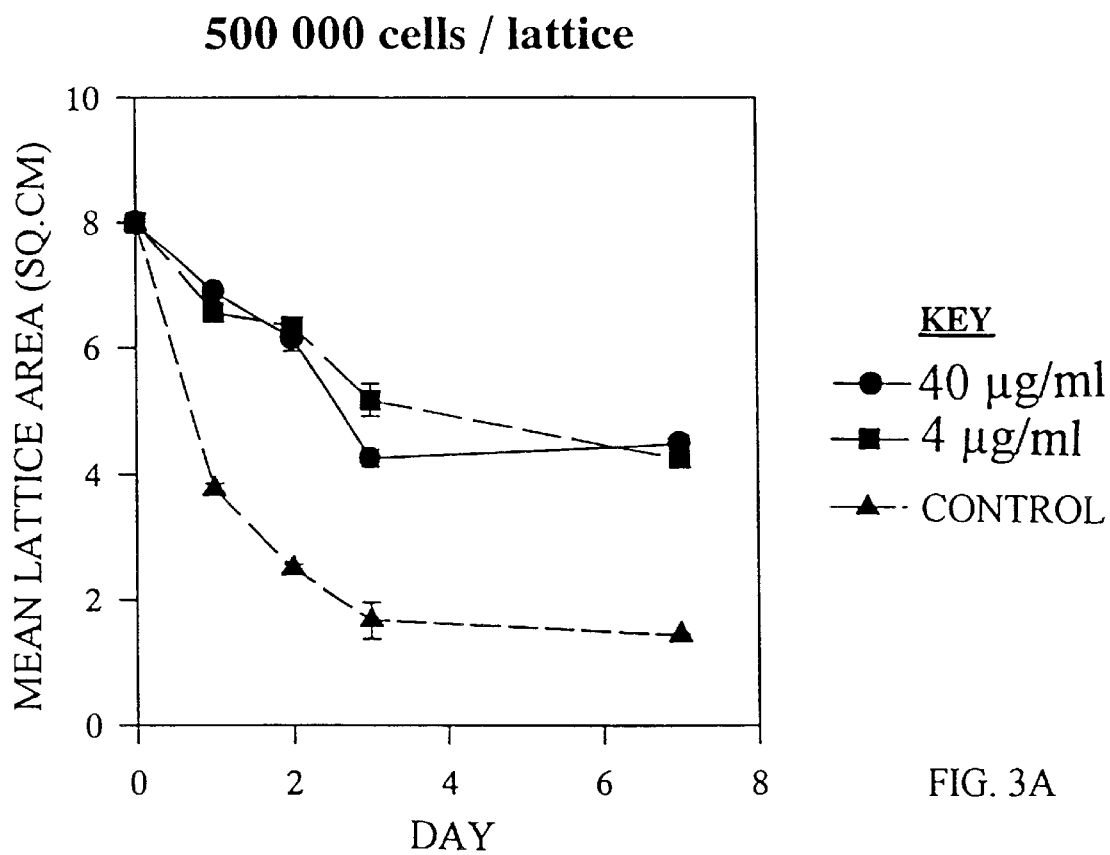
FIG. 3A is a diagrammatic representation of the results of experiments described in Example 3(a). It is a graph showing mean lattice area of fibroblast populated collagen gels over time for different culture regimes.
Figure 3B:
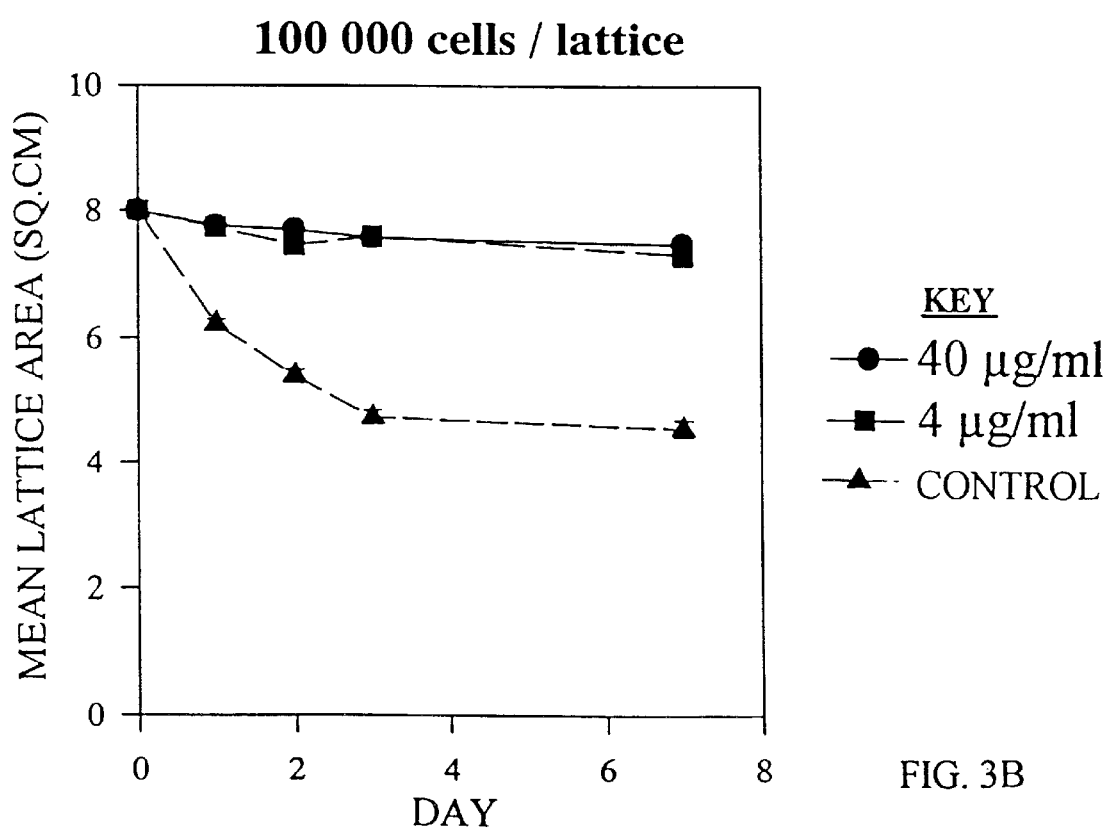
FIG. 3B is a diagrammatic representation of the results of experiments described in Example 3(a). It is a graph showing mean lattice area of fibroblast populated collagen gels over time for different culture regimes.

For results, see FIGS. 3A and 3B.

FIG. 3A shows the results for the collagen lattices (gels) populated with 500,000 cells per lattice. The mean lattice area is plotted against time (in days) for gels treated with each of the three solutions. As may be seen, the contraction of the gels exposed to inhibitor solutions is much less than that of gels exposed to the control solution. FIG. 3B shows the results for the collagen lattices populated with 100,000 cells per lattice. Again the mean lattice area is plotted against time for each of the three regimes. As may be seen, the contraction of the gels exposed to inhibitor solutions is much less than that of gels exposed to control solutions. Comparing FIGS. 3A and 3B shows that the contraction of lattices populated with 500,000 cells per lattices is greater than that of lattices populated with 100,000 cells under the same conditions.

Discussion

The experiments confirmed that contraction is stronger when there is a higher cell concentration and that the same dose of inhibitor cannot then provide such good inhibition as when there is a lower cell concentration.
b) Reversibility Collagen gels were prepared and seeded with fibroblasts ($1\times10^5$ cells/lattice (gel)) as described in Example 1 above. They were exposed to inhibitor and control solutions in the following ways:

(i) continual exposure to control solution (medium containing hydroxamic acid);

(ii) continual exposure to inhibitor solution (medium containing 4 µg/ml Galardin);

(iii) continual exposure to inhibitor solution (as (b)) until day 14 post seeding and then replacement by control solution (as (a));

(iv) lattices were allowed to contract for 5 days and then were continually exposed to control solution (as (a)) for 25 days;

(v) lattices were allowed to contract for 5 days and then were continually exposed to inhibitor solution (as (b)) for 25 days;

(vi) lattices were allowed to contract for 5 days and then were continually exposed to inhibitor solution (medium containing 40 µg/ml Galardin) for 25 days.

The test solutions were made up in accordance with Example 1 (c) and the growth medium in the cultures was changed every 3 to 4 days.

Figure 3C:
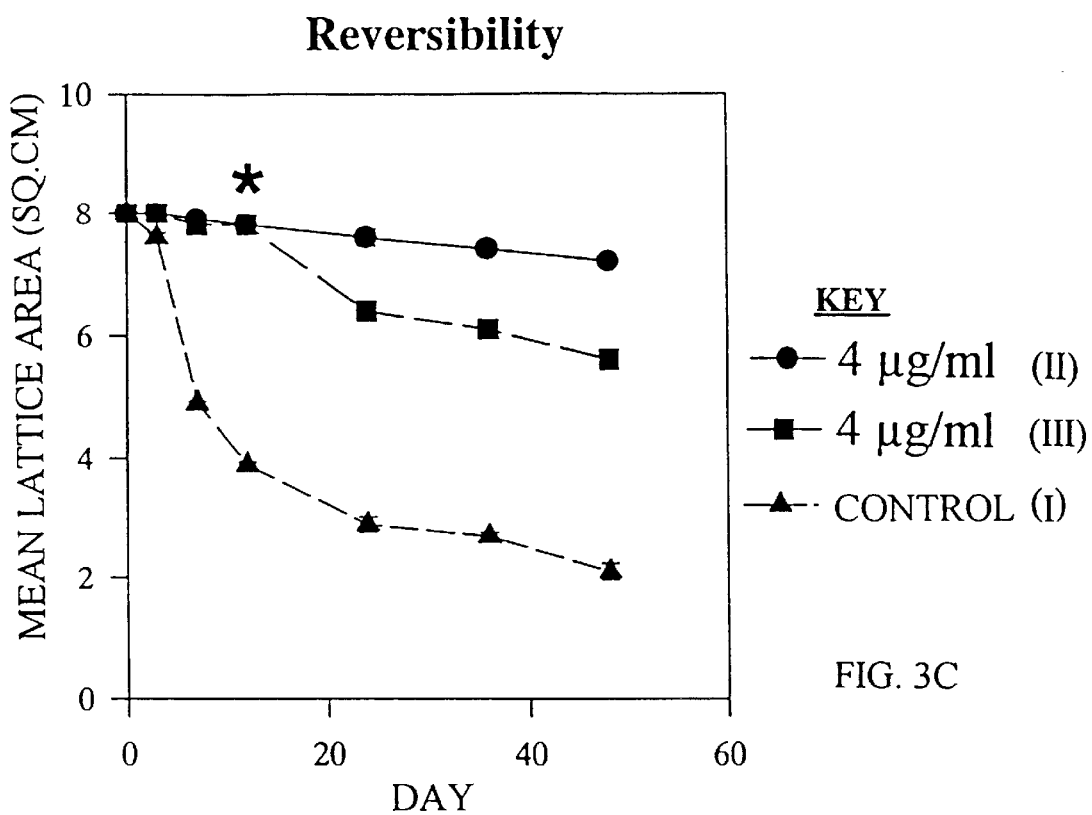
FIG. 3C is a diagrammatic representation of the results of experiments described in Example 3(b). It is a graph showing mean lattice area of fibroblast populated collagen gels over time for different culture regimes.
Figure 3D:
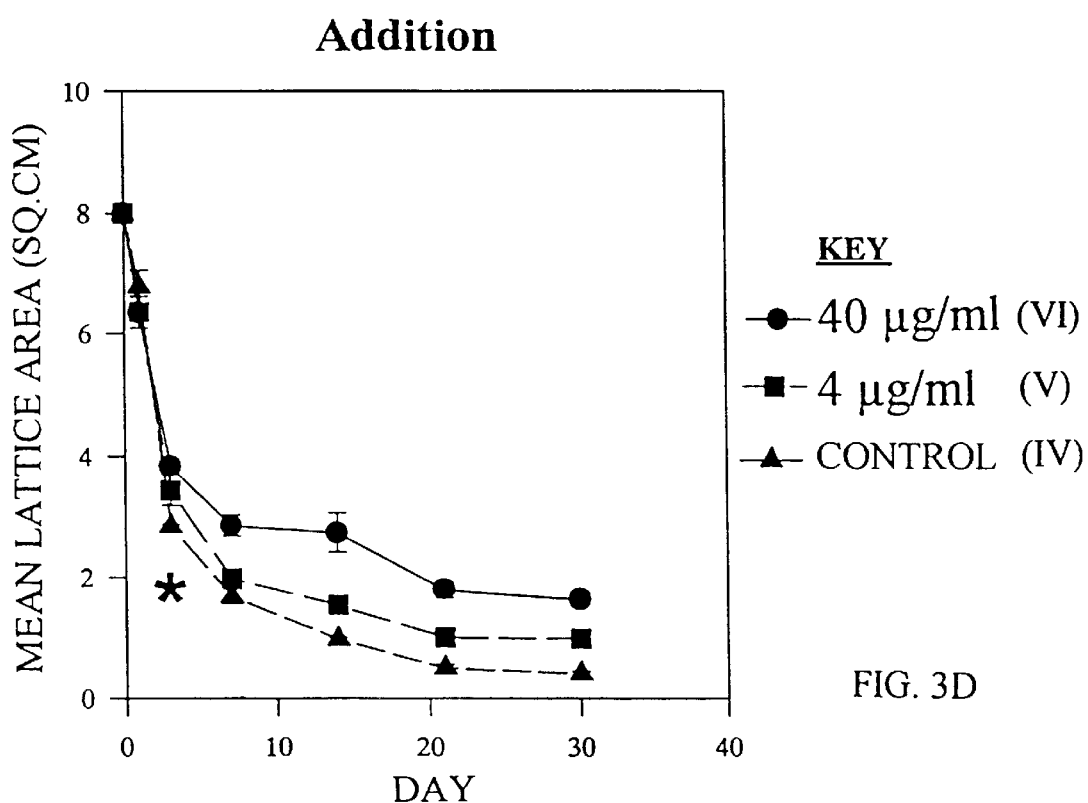
FIG. 3D is a diagrammatic representation of the results of experiments described in Example 3(c). It is a graph showing mean lattice area of fibroblast populated collagen gels over time for different culture regimes.

The results of (i), (ii) and (iii) are shown in FIG. 3C and the results of (iv), (v) and (vi) are shown in FIG. 3D.

FIG. 3C is a plot of mean lattice area against time showing the results for experiments (i), (ii) and (iii). As may be seen, the mean area of lattices treated with control solution decreases from day 0; contraction occurs for the whole period. For the lattices initially treated with inhibitor solutions there is very little contraction and in the case where the lattices continue to be exposed to inhibitor (ii) the reduction in mean area is low even after 40 to 50 days. For the lattices exposed to inhibitor solution until day 14 (shown as * in FIG. 3C) and thereafter exposed to control solution (experiment (iii)) there is a significant increase in contraction from day 14 onwards.

FIG. 3D is a plot of mean lattice area against time for each of experiments (iv), (v) and (vi). As may be seen, in the first 5 days of the experiments when lattices were not exposed to test solutions the lattices underwent substantial contraction. After day 5 (marked as * in FIG. 3D) the lattices were exposed to the test solutions. The contraction continued (there was no reversal) but at a reduced rate. Both the 4 µg/ml and 40 µg/ml solutions of Galardin inhibited contraction in comparison with the control solution. The 40 µg/ml solution of Galardin gave a stronger inhibitory effect than the 4 µg/ml solution.

Discussion

Experiments (i), (ii) and (iii) showed that exposure to inhibitor solution inhibited contraction in comparison with exposure to the control solution and that when the inhibitor solution was then replaced by control solution the rate of contraction increased, i.e. inhibition stopped. Hence the inhibition is reversible.

Experiments (iv), (v) and (vi) showed that even when contraction of the gels had been allowed to take place for 5 days without any type of inhibition, the addition of inhibitor solutions still gave inhibition of contraction. The more concentrated inhibitor solution gave greater inhibition.

c) Cytotoxicity

Figure 3E:
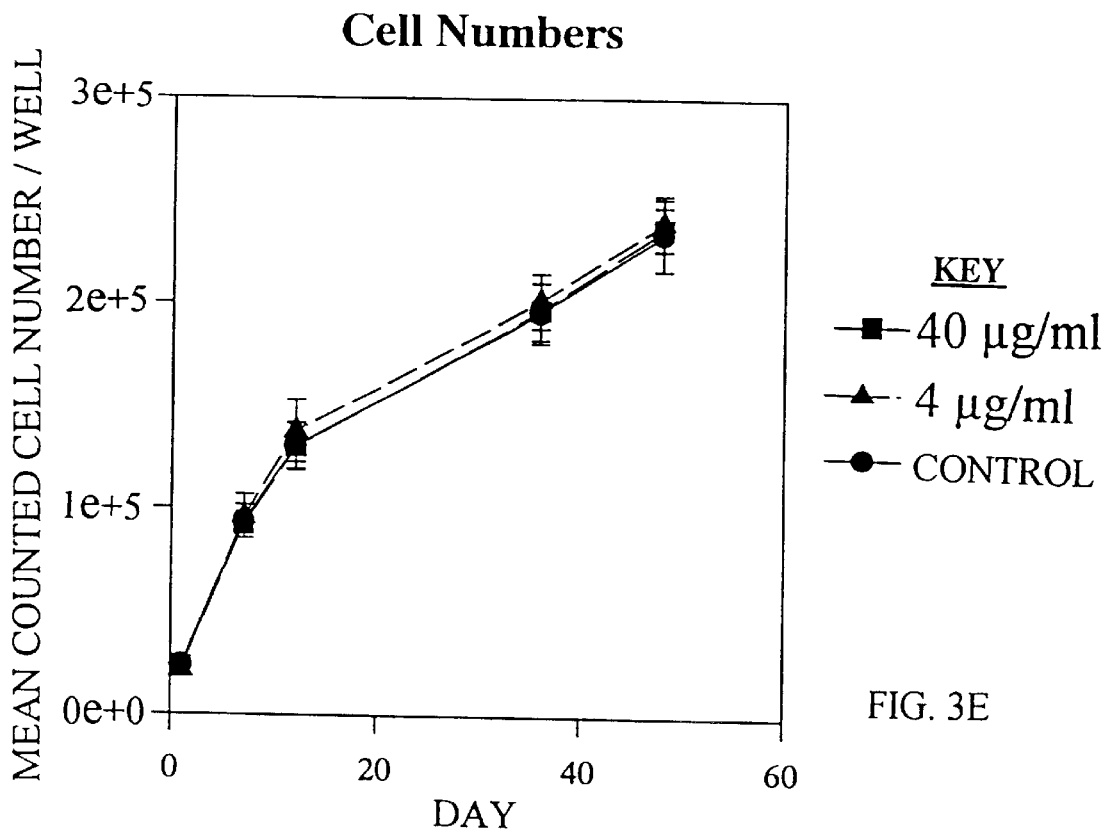
FIG. 3E is a diagrammatic representation of the results of experiments described in Example 3(c). It is a graph showing the mean number of cells per well against time under a number of different culture regimes.
Figure 3F:
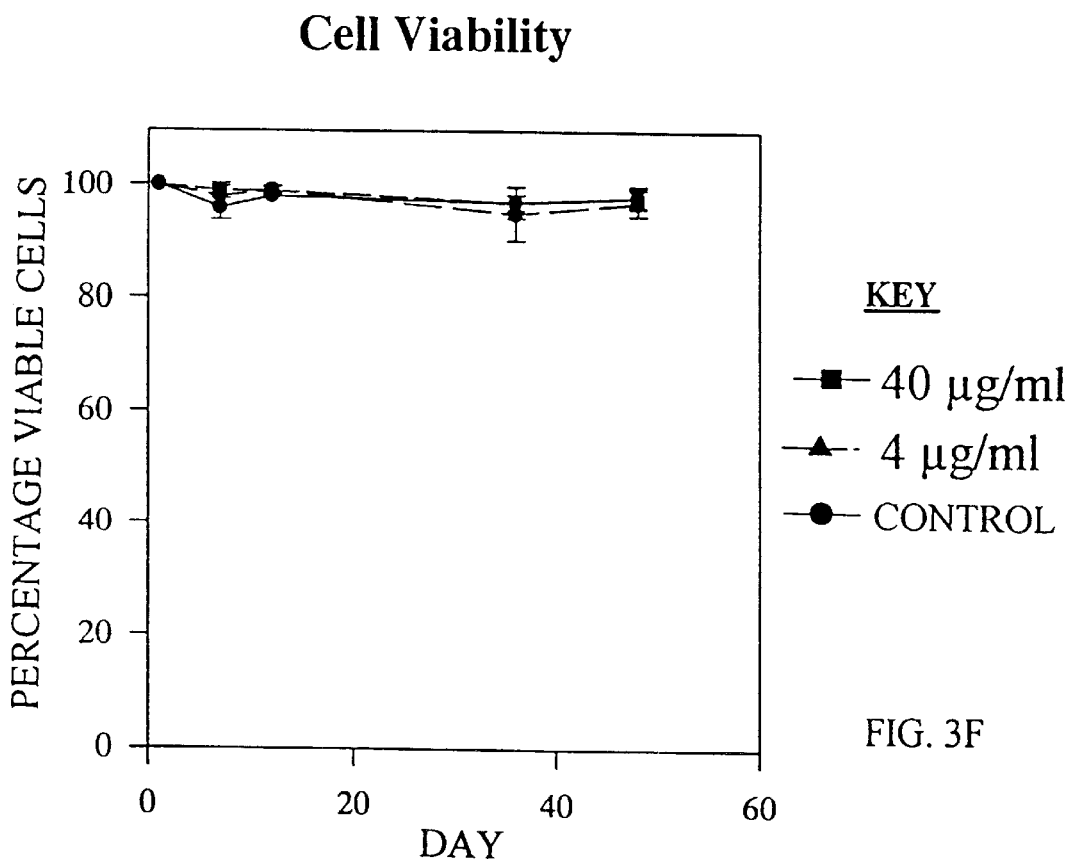
FIG. 3F is a diagrammatic representation of the results of experiments described in Example 3(c). It is a graph showing the percentage of viable cells against time under a number of different culture regimes.

This experiment was carried out substantially according to the method of Example 2, except that cells were seeded at $2\times10^4$ cells per well, cultured without radioactive material and were exposed to control medium (DMEM/10% NCS) or Galardin at 40 µg/ml and 4 µg/ml concentration. Approximately 1 ml of test solution was added in each case. Wells were harvested and cells counted on a haemocytometer, see FIG. 3E for the results, and the percentage of viable cells in each well was measured using the trypan blue dye exclusion test, see FIG. 3F for the results. As can be seen the Galardin did not adversely affect cell viability and number compared to controls.

Discussion

It appears that MMP inhibitors may be used in quantities and concentrations high enough to restrict contraction without significant toxicity.

d) BB-94

Figure 3G:
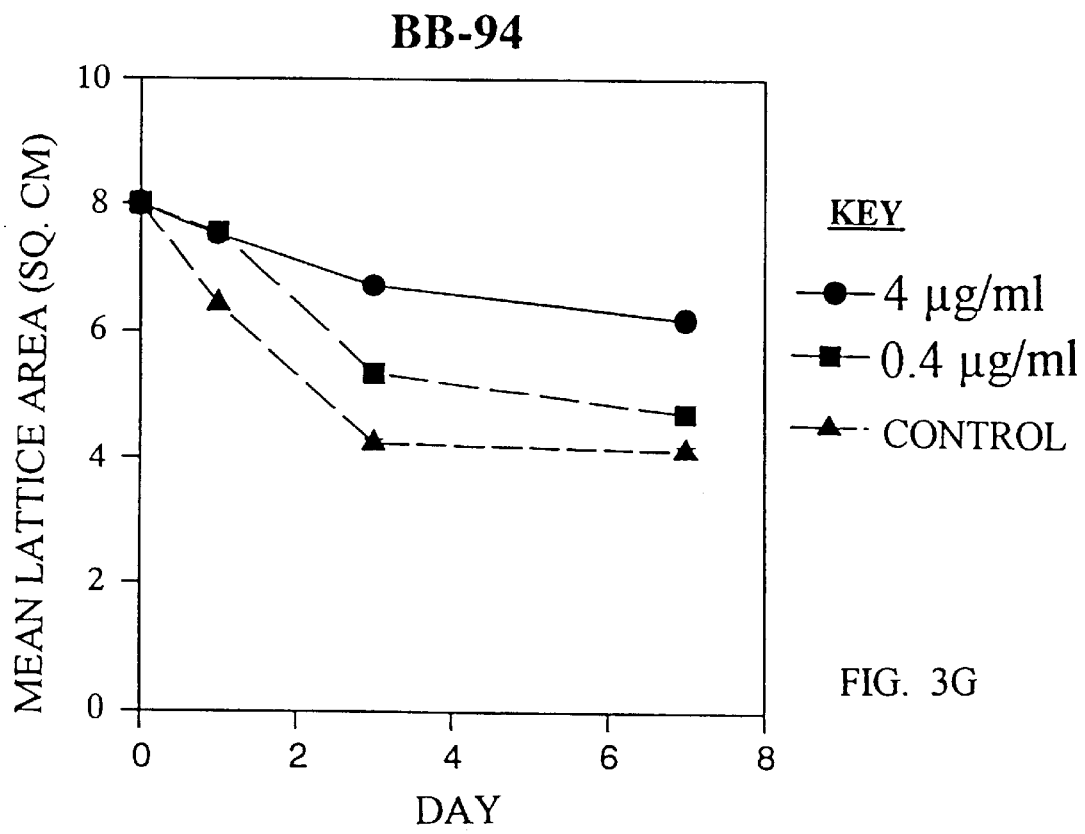
FIG. 3G is a diagrammatic representation of the results of experiments described in Example 3(d). It is a graph showing mean lattice area of fibroblast populated collagen gels over time for different culture regimes.

The experiment was carried out as for (a) above with $1\times10^5$ cells per lattice and the test solutions used were BB-94 4 µg/ml, BB-94 0.4 µg/ml and control with vehicle (0.1% vol/vol DMSO). The development of the lattices was followed for seven days after seeding. For the results see FIG. 3G, from which it is clear that BB-94 gave significant inhibition of contraction.

e) Antibodies

The experiment was carried out as for (d) above except that the test solutions used were 1:50 (vol/vol) of antibodies in growth medium. The antibodies used were antibodies to MMPs 1, 2, 3 and 9, obtained from Biogenesis Ltd., (Poole, U.K.). A control solution of 0.1% sodium azide and 0.14% rabbit serum in PBS diluted to 1:50 in growth medium was also used. See FIG. 3H for the results.

Figure 3H:
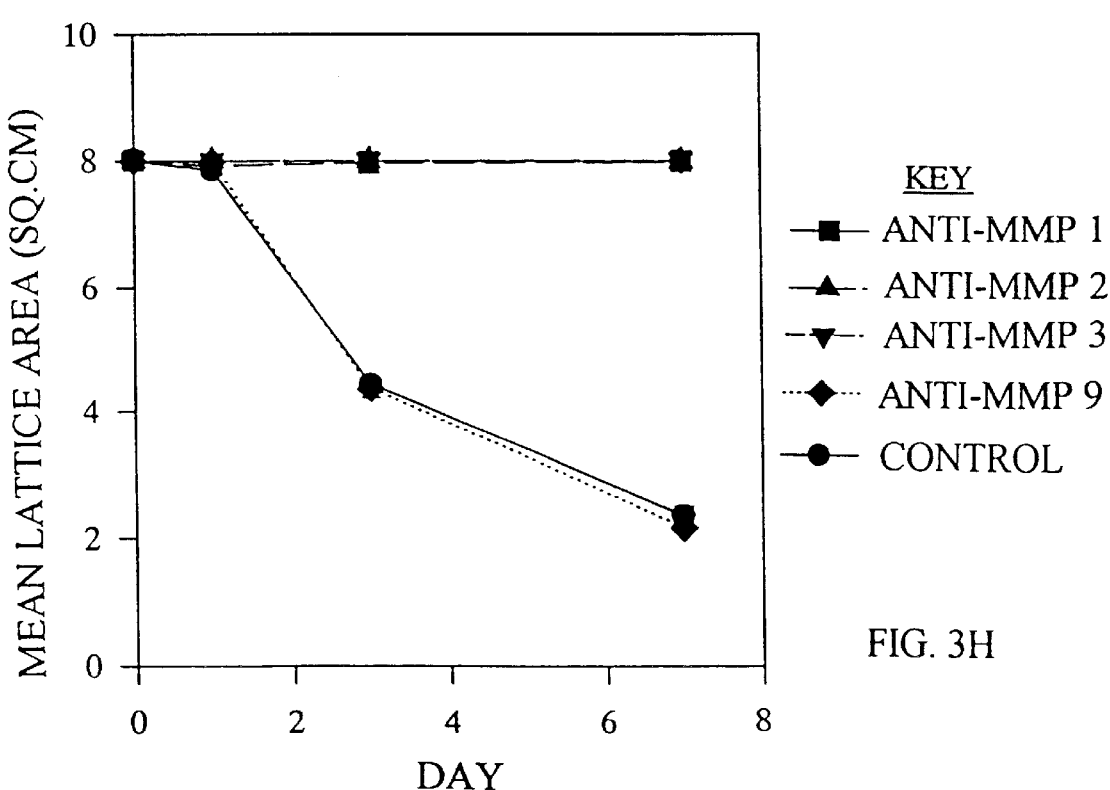
FIG. 3H is a diagrammatic representation of the results of experiments described in Example 3(c). It is a graph showing mean lattice area of fibroblast populated collagen gels over time for different culture regimes.

FIG. 3H is a plot of mean lattice area against time for lattices exposed to each of the test solutions. As may be seen, the lattices exposed to control solution and to the solution of antibody to MMP9 showed significant contraction. The lattices exposed to one of the antibodies to MMP1, MMP2 or MMP3 showed no significant contraction.

Discussion

As may be seen from FIG. 3H significant inhibition was achieved with antibodies for MMPs 1, 2 and 3 but not with the antibody for MMP9. This therefore shows that antibodies may act as satisfactory MMP inhibitors for use in inhibiting contraction. It also appears that while MMPs 1, 2 and 3 may all be involved in the contractile process MMP9 is not.

Example 4

A series of experiments were carried out in which the MMP mRNA and protein production of human Tenon's capsule fibroblasts, under a number of conditions, was analysed.

Fibroblast cells were both grown in monolayer culture and were seeded in collagen lattices. Total RNA was isolated from samples containing $3\times10^6$ cells using the method described in Chomczynski & Sacchi 1987. Samples were taken from cells in monolayer culture on day 0 of the experiment and samples were also taken from cells, which were contracting collagen lattices after 9 hours, 1 day and 7 days.

1 µ/mg samples of the RNA were treated with known copy numbers of a synthetic RNA template (0.1 to 100,000 copies) containing complementary sequences to the primers for sequences to MMPs 1, 2, 3 and 9. The mixtures underwent reverse transcriptase reactions prior to amplification by PCR using specific primers for MMPs 1, 2, 3 and 9. During the PCR reaction both the sample RNA and the synthetic template RNA compete equally for primer binding.

Band intensities were image analysed and the ratio of amplified synthetic template to amplified sample intensities calculated. These values were plotted versus initial template copy number. When the ratio of amplified synthetic template to sample is one, then the initial copy numbers of synthetic template and sample are equal. This allowed calculation of message copy number per cell in all samples.

Samples of conditioned medium and collagen lattices ($1\times10^5$ cells/lattice) were collected on days 1, 3 and 7 post seeding. Lattices were washed in phosphate buffered saline (PBS; 3×3 ml) prior to homogenisation in 0.5% (vol/vol) Triton-X100 in PBS [Hunt et al. 1993]. Gelatin zymography [Heussen & Dowdle 1980] was then performed on these samples. Briefly, samples and prestained molecular weight standards were resolved on 10% tris glycine gels containing 0.1% gelatin (Novex, R&D Systems, Oxford, U.K.). Gels were then incubated for 30 minutes in renaturing buffer, 30 minutes in developing buffer followed by a further 18 hours in developing buffer at 37° C. (all Novex). Gels were than stained in 0.5% (wt/vol) commassie blue in 45% (vol/vol) water, 45% (vol/vol) methanol and 10% (vol/vol) glacial acetic acid, followed by destaining in 45% (vol/vol) water, 45% (vol/vol) water, 45% (vol/vol) methanol and 10% (vol/vol) glacial acetic acid. MMP activity appeared as clear bands on a blue background.

Results

The experiments showed that the RNA extracted from cells which were contracting collagen contained raised levels of mRNA for MMPs 1, 2 and 3 but not 9, in comparison with that taken from cells in monolayer cultures. They also showed that levels of MMP mRNA decreased over the 7 day culture period.

|     | mRNA Copy Number/$10^6$ Cells | | | |
| --- | --- | --- | --- | --- |
| MMP | Monolayer | 9 Hours | 1 Day | 7 Days |
| 1 | 8 | 71 | 143 | 3 |
| 2 | <1 | 15 | 144 | 81 |
| 3 | <1 | 18 | 132 | 16 |
| 9 | <1 | <1 | <1 | <1 |

Figure 6:
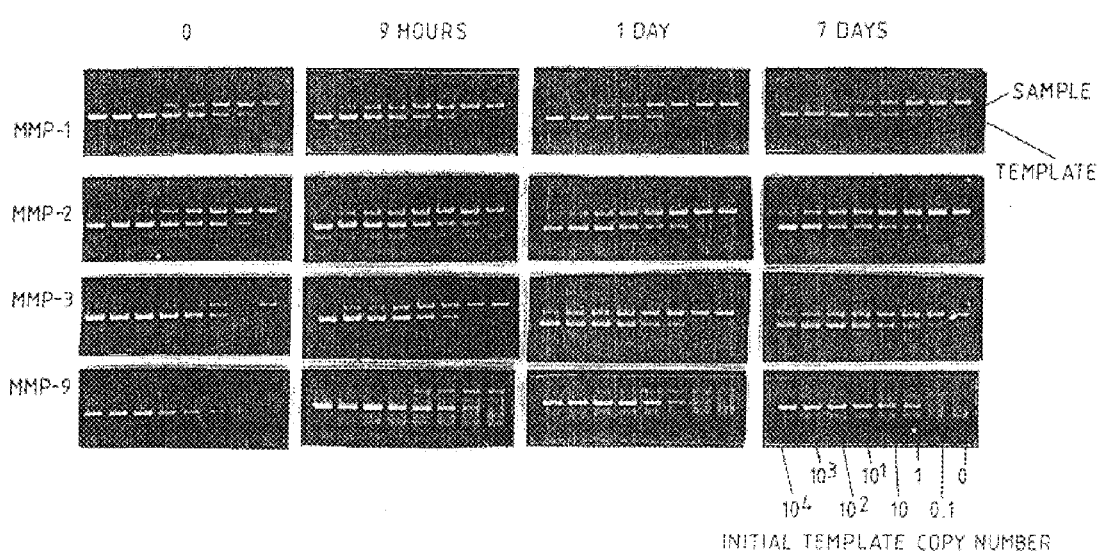
FIG. 6 is a reproduction of a photograph showing the results of the PCR reactions described in Example 4.

Also see FIG. 6 for results. FIG. 6 is a reproduction of a photograph of the results of the PCR reaction. It shows the sample and template bands at day 0, 9 hours, 1 day and 7 days for mRNA encoding each of MMPs1, 2, 3 and 9.

Figure 7:
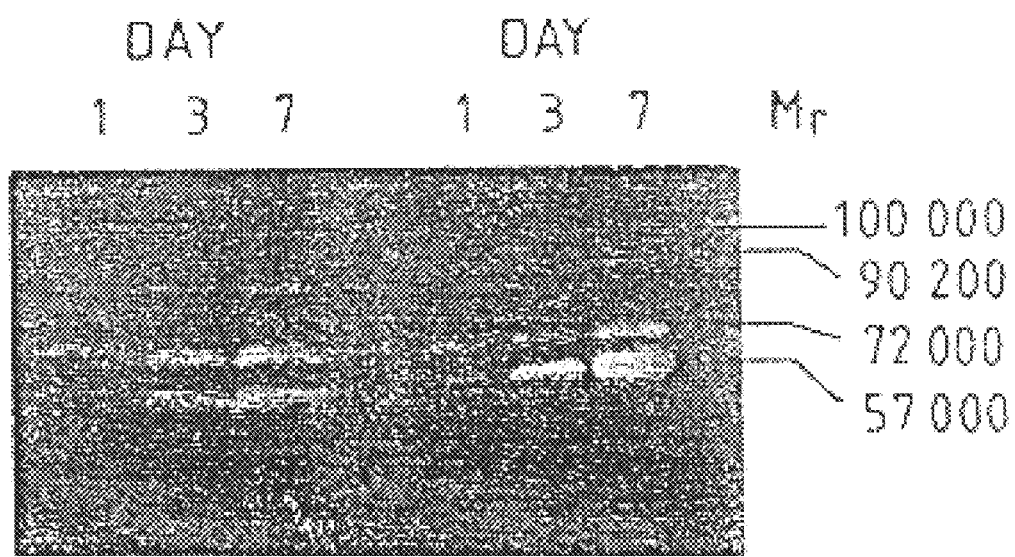
FIG. 7 is a reproduction of a photograph showing the results of the gelatin zymography analyses described in Example 4.

The gelatin zymography showed that actively contracting cells when compared to cells from monolayer cultures produced four proteolytically active species (Mr approximately 100,000; 90,200; 72,000 and 57,000), two of which appear (ones with Mrs of 72,000 and 57,000) to increase over the 7 day period. See FIG. 7 for results. One was activated upon incubation with aminophenyl mecuric acetate (Mr 100,000 reduced to 57,000).

Discussion

The experiments showed that both MMP mRNA and protein production by ocular fibroblasts is dramatically increased upon culture within, and during the contraction of, a three dimensional collagen matrix. It therefore appears that active production of MMPs occurs during the contractile process.

Further experiments showed that treatment of seeded lattices with Galardin resulted in the abolishment of the four proteolytically active species.

Example 5

This series of experiments investigated the effect of MMP inhibitors on the degree of contraction of collagen lattices by fibroblasts from various tissue sites and species.

Collagen lattices (gels) were prepared as previously described in Example 1 and were seeded with $1 \times 10^5$ cells per lattice of:

i) human dermal fibroblasts;

ii) rat parietal sheath fibroblasts; or iii) rat endotendon fibroblasts.

The lattices were then exposed to growth medium containing Galardin at 40 μg/ml or hydroxamic acid at 100 μM (control). The test solutions were made up as described in Example 3 above and approximately 3 ml dose of the appropriate test solutions were used. The area of each lattice was measured over 7 days and the results are shown in FIGS. 4A, 4B and 4C.

Figure 4A:
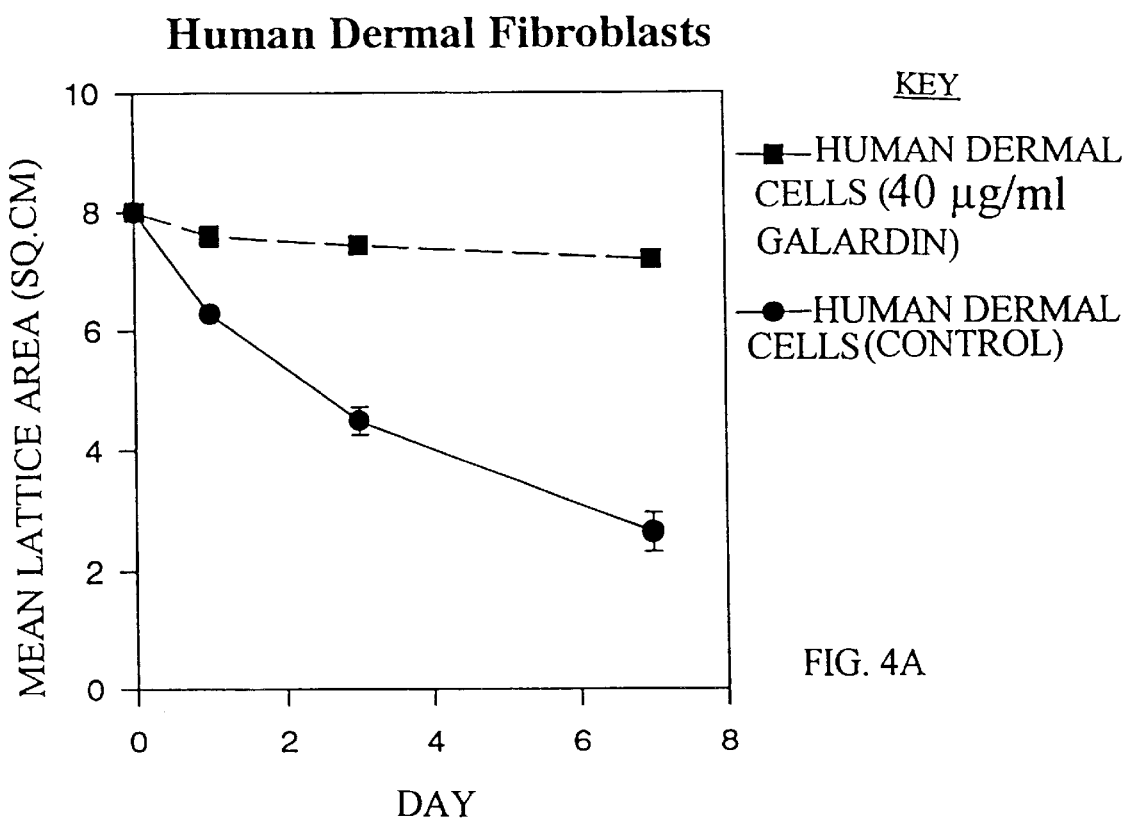
FIG. 4A is a diagrammatic representation of the results of the experiments described in Example 5(i). It is a graph showing the mean lattice area of fibroblast populated collagen gels over time under two different culture regimes.
Figure 4B:
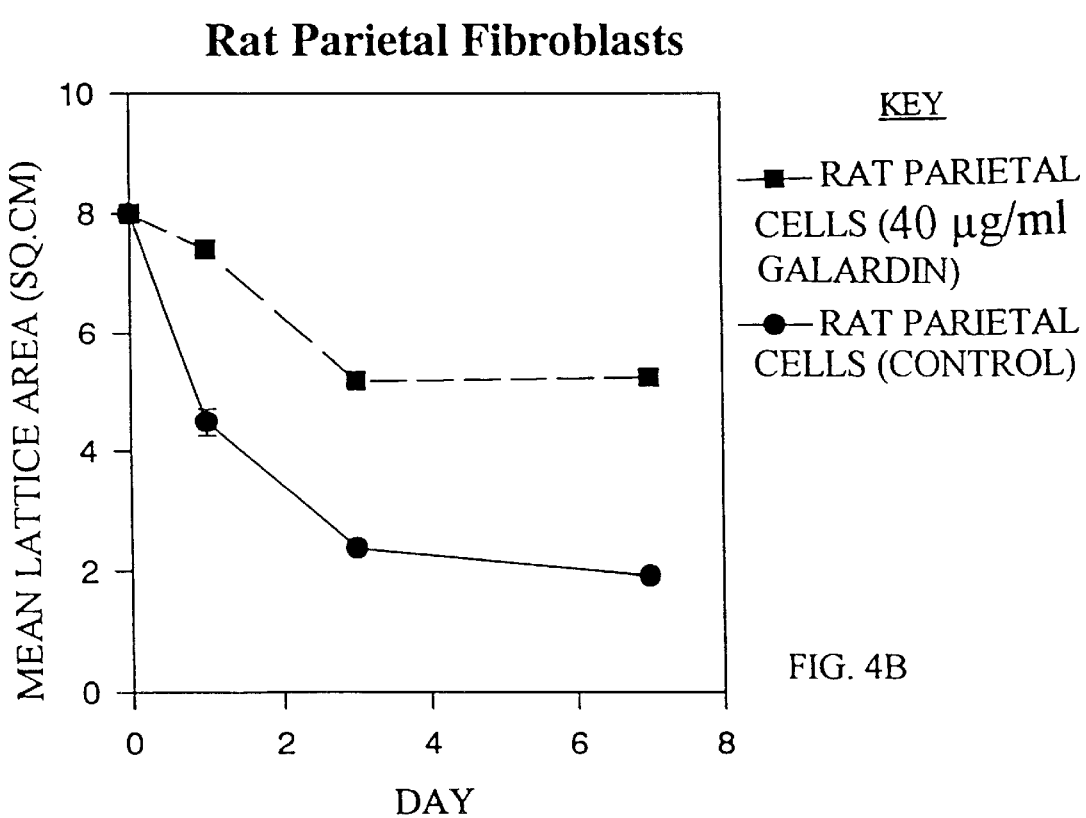
FIG. 4B is a diagrammatic representation of the results of the experiments described in Example 5(ii). It is a graph showing the mean lattice area of fibroblast populated collagen gels over time under two different culture regimes.
Figure 4C:
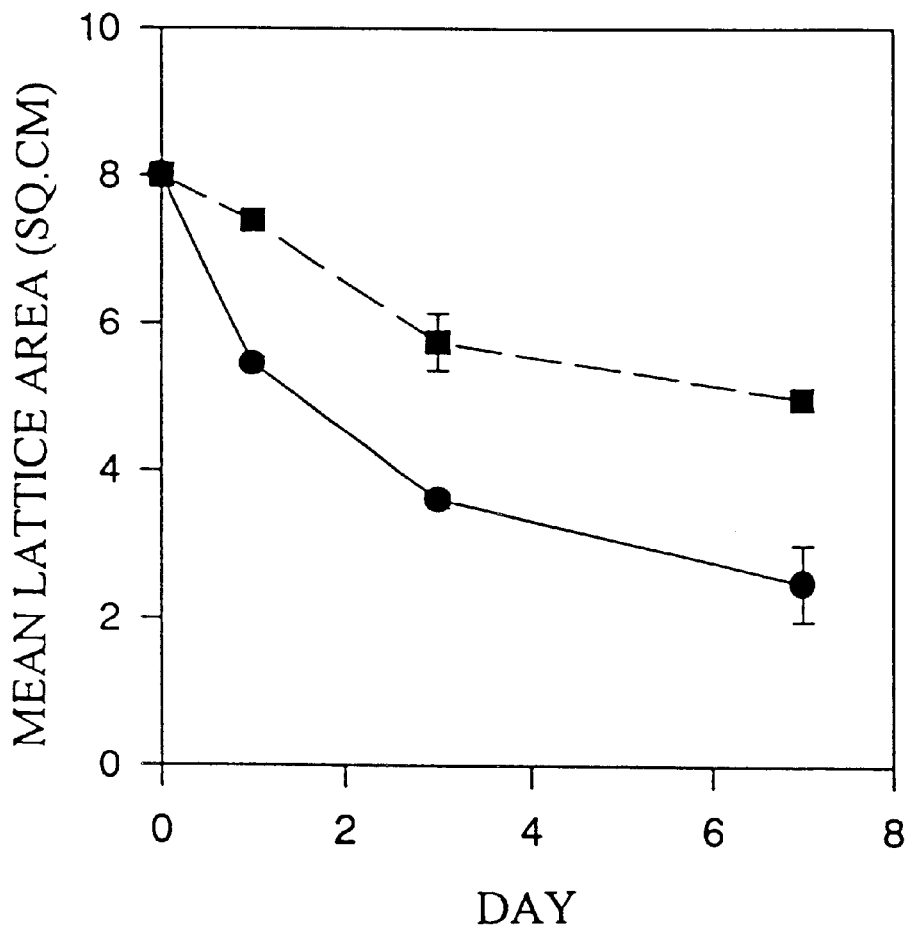
FIG. 4C is a diagrammatic representation of the results of the experiments described in Example 5(iii). It is a graph showing the mean lattice area of fibroblast populated collagen gels over time under two different culture regimes.

FIGS. 4A, 4B and 4C are plots of mean lattice area over time for lattices populated with fibroblasts under exposure to either control solution or inhibitor solution. FIG. 4A for human dermal fibroblasts, 4B for rat parietal sheath fibroblast and 4C for rat endotendon fibroblast. As may be seen, the contraction of lattices populated with any of the three types of fibroblasts was greatly reduced when exposed to the inhibitor solutions in comparison with the lattices populated with the same type of fibroblasts and exposed to the control solution.

Discussion

Exposure to the inhibitor resulted in a significant degree of inhibition of contraction compared to controls in all of the cell types. In each case, inhibition of contraction was accompanied by a decreased cellular invasion into and migration through, the surrounding matrix compared to controls. Therefore it appears that inhibition of cellular invasion is an important mechanism of MMP inhibitor action.

Example 6

The effect of an MMP inhibitor on the contraction of an artificial skin equivalent was tested. A collagen lattice (gel) was prepared as in Example 1 and was seeded with both human keratinocytes and human dermal fibroblasts to mimic skin. This lattice was then exposed to growth medium containing Galardin at 40 μg/ml or hydroxamic acid at 100 μM (control). The solutions were made up as described in Example 3(a) above and approximately 3 ml portions of the appropriate solutions were used. The lattice area was measured over 7 days and the results are shown in FIG. 5.

Figure 5:
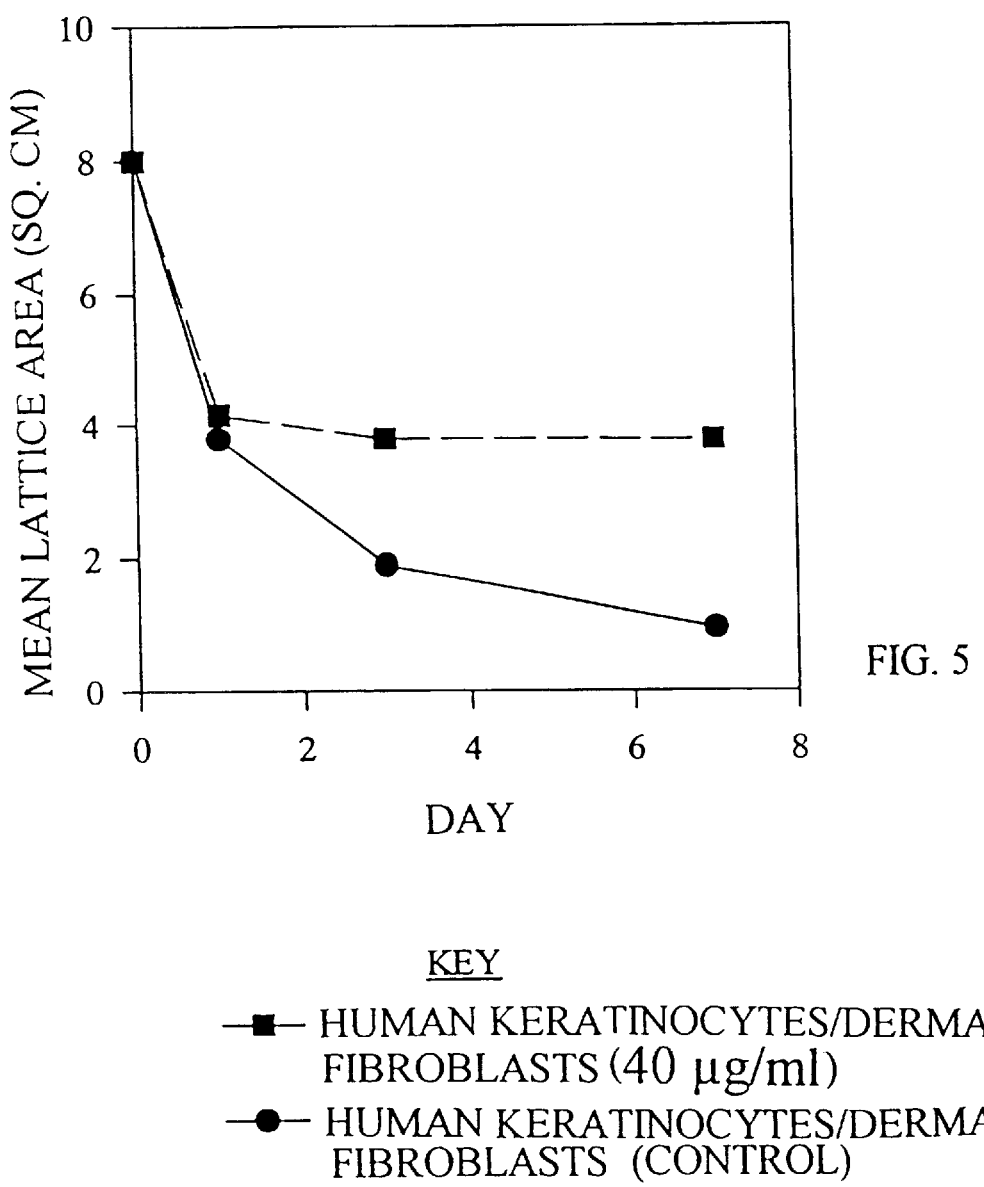
FIG. 5 is a diagrammatic representation of the results of the experiments described in Example 6. It is a graph showing the mean lattice area of fibroblast populated collagen gels over time under two different culture regimes.

FIG. 5 is a plot of the mean lattice area over time (in days) for lattices exposed to the control solution and for lattices exposed to the inhibitor solution. As may be seen, the lattices exposed to the inhibitor solution suffered less contraction than those exposed to the control solution.

Discussion

It is therefore possible to inhibit the contraction of a collagen gel with fibroblasts and epithelial cells, i.e. an approximate model of skin.

Example 7

The effects of MMP inhibitors on ocular fibroblast morphology within collagen lattices were studied in this series of experiments.

Collagen lattices seeded with ocular fibroblasts were prepared and exposed to MMP inhibitors, both synthetic chemicals and antibodies, as described in Example 3 above. Cellular morphology was monitored by phase contrast microscopy.

Cells populating control collagen lattices exhibited stellate (S) and bipolar (B) morphology by 7 days post seeding. Small cytoplasmic projections were exhibited by cells exposed to 4 μg/ml Galardin, 4 μg/ml BB-94, antibody to MMP1 or MMP2 at 7 days post seeding. Cells exposed to MMP3 antibody did not produce any cytoplasmic projections into the surrounding matrix. Exposure to antibody to MMP9 did not affect morphology compared to controls.

Discussion

These results showed that cells populating lattices exposed to Galardin, BB-94 and antibodies to MMPs 1, 2 and 3 exhibited decreased invasion into the surrounding collagen matrix compared to controls and to cells exposed to an antibody to MMP9. This decrease in invasion into the matrix was always accompanied by the inhibition of both lattice contraction and migration through the matrix. This again showed that inhibition of invasion is important.

Example 8

This series of experiments was designed to investigate the effects of an MMP inhibitor (Galardin) on Tenons capsule fibroblast cellular processes required for collagen contraction.

Monolayer cultures of fibroblasts and collagen lattices (gels) seeded with $1 \times 10^5$ cells per lattice were prepared (as described in Example 1).

Figure 8A:
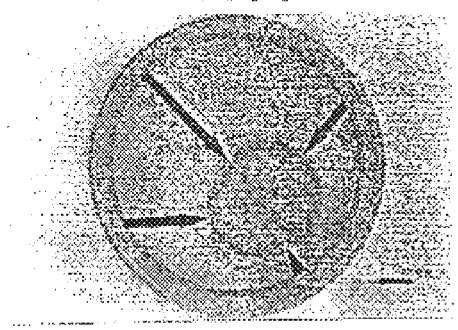
FIG. 8A and FIG. 8B are each a reproduction of a photograph of a collagen gel seeded with fibroblasts showing the degree of contraction as described in Example 8.
Figure 8B:
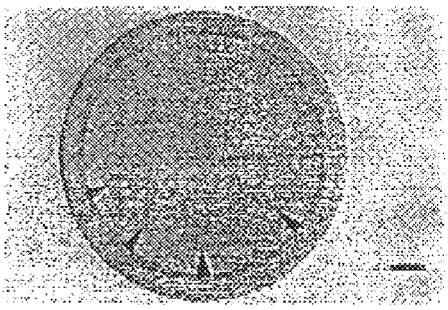

The degree of contraction of collagen gels treated with control solution and with inhibitor solution containing 40 μg/ml Galardin (solutions were made up as described in Example 1 and approximately 3 ml portions of solutions were used) was monitored, as described above. FIG. 8A shows the degree of lattice contraction of a control gel 7 days post seeding and FIG. 8B shows the degree of contraction of the gel which was exposed to inhibitor solution.

Figure 9A:
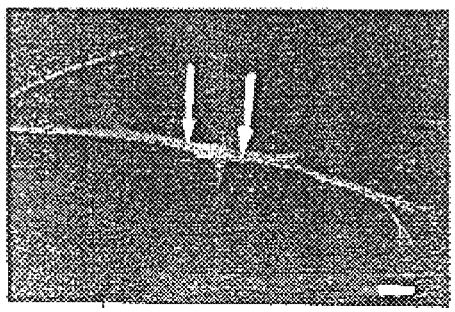
FIG. 9A and FIG. 9B are each a reproduction of a photograph of a collagen gel seeded with fibroblasts showing the development of actin stress fibres on the surface of the cells as described in Example 8.
Figure 9B:
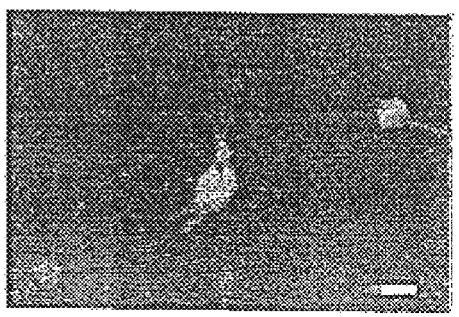

The actin cytoskeleton of cells in lattices and in monolayer culture was immunofluorescently stained with FITC-phalloidin [Martin & Lewis 1992]. See FIGS. 9A (control) and 9B (exposed to inhibitor). The arrows indicate the actin stress fibres on the surface of the cells populating the collagen gels. These fibres are clearly present in the control but do not appear to be present in the lattice that was exposed to inhibitor solution.

Figure 10A:
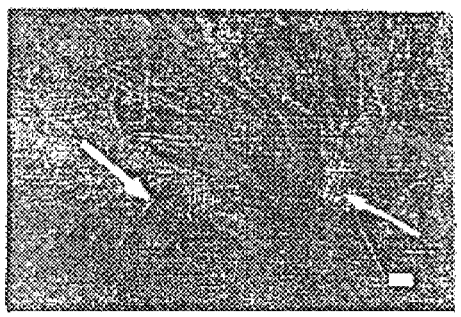
FIG. 10A and FIG. 10B are each a reproduction of a photograph of fibroblasts grown in monolayers showing the presence of stress fibres as described in Example 8.
Figure 10B:
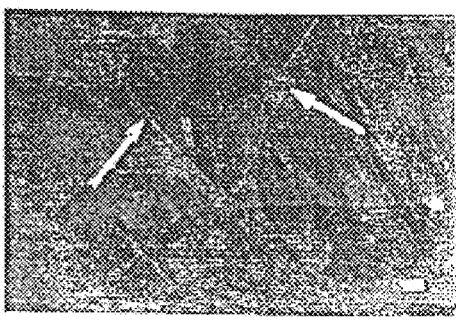

Differences between the controls and those exposed to inhibitor (40 μg/ml Galardin) were seen. In order to assess whether this difference was owing to the direct effect of the inhibitor or to differences in the degree of invasion into the matrix, cells were exposed in monolayer culture to the inhibitor and the cytoskeleton was stained. See FIG. 10A (control) and 10B (exposed to inhibitor). The arrows indicate the stress fibres on the cells in the monolayer culture. As may be seen, they are present in both the control monolayer culture and in the monolayer culture exposed to the inhibitor solution.

The inhibitor did not appear to affect the actin cytoskeleton compared to controls in monolayer culture.

Figure 11A:
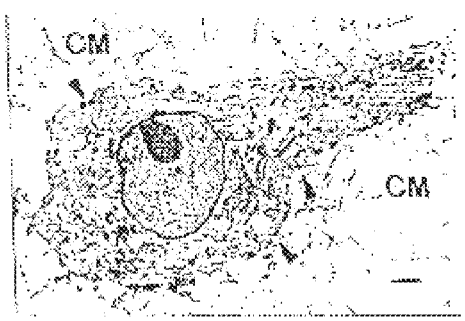
FIG. 11A and FIG. 11B are each a reproduction of a photograph of a collagen gel seeded with fibroblasts showing cellular attachments as described in Example 8.
Figure 11B:
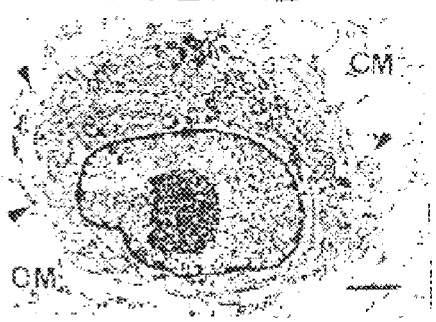

Lattices for transmission electron microscopy were harvested 3 days post seeding, washed with PBS (3×3 ml), and fixed overnight at 4° C. in 2.5% (vol/vol) glutaraldehyde with 0.5% (wt/vol) tannic acid in 0.07M sodium cacodylate buffer (pH 7.0). Following a rinse in 0.01M cacodylate-HCl buffer (pH 7.3), postfixation for 2 hours in 1% (wt/vol) aqueous osmium tetroxide at 4° C., lattices were dehydrated through ascending alcohols and cleared in propylene dioxide. Samples were then infiltrated with propylene dioxide/araldite (1:1 vol/vol) for 1 hour, followed by 12 hours immersion in Araldite (trade mark) alone. Samples were then embedded in fresh Araldite, ultrathin sections cut and sequentially stained with saturated uranyl acetate followed by Reynolds lead citrate. See FIGS. 11A (control) and 11B (exposed to inhibitor). The arrow heads indicate the cellular attachments to the collagen matrix. It is clear that the attachment of the fibroblasts to their surrounding collagen matrix was not affected by the inhibitor.

Discussion

These experiments showed that Galardin did not affect the cytoskeleton or cell matrix attachment of the fibroblasts. Effects on the cytoskeleton or on cell matrix attachment were possible explanations for the effect of Galardin on contraction and therefore for the effect of MMP inhibitors on contraction.

GENERAL DISCUSSION

A number of studies have suggested possible mechanisms for cell mediated collagen contraction. A number of workers have suggested that MMPs are not produced or are produced during lattice contraction but are not implicated in the contractile process. The above-described experiments demonstrate that cellular derived MMP activity is crucial to the process of collagen contraction. The requirement of MMP activity for contraction appears to be common to all of the fibroblasts tested.

The present invention is not to be limited in scope by the embodiments disclosed in the Examples which are intended to illustrate the invention. Indeed, various modifications of the invention in addition to those shown and described herein will become apparent to those skilled in the art and are intended to fall within the scope of the appended claims.

Bibliography

Eisen A. Z., Block K. L., Sakai T., Inhibition of human skin collagenase by human serum, J. Lab. Clin. Med. 1976; 75: 258–263.

Vater C. A., Mainardi, C. L., Harris E. D. Jr, Native cross-links in collagen fibrils induce resistance to human synovial collagenase. Biochem. J. 1979; 181: 639–645.

Stricklin G. P., Welgus H. G., Bauer E. A., Human skin collagenase in recessive dystrophic epidermolysis bullosa: Purification of a mutant enzyme from fibroblast cultures. J. Clin. Invest. 1983; 69: 1373–1383.

Murphy G., McGuire M. B., Russell R. G. G., Reynolds J. J., Characterization of collagenase, other metalloproteinases and an inhibitor (IMP), produced by human synovium and cartilage in culture. Clinical Science 1981; 61:711–716.

Welgus H. G., Kobayashi D. K., Jeffrey J. J., The collagen substrate specificity of rat uterus collagenase. J. Biol. Chem. 1983; 258 : 14162–14165.

Welgus H. G., Stricklin G. P., Human skin fibroblast collagenase inhibitor: comparative studies in human connective tissues, serum and amniotic fluid. J. Biol. Chem. 1983; 258 : 12259–12264.

Bar-Shavit Z., Teitelbaum S. L., Stricklin G. P., Eisen A. Z., Kahn A. J., Welgus H. G., Differentiation of human leukemia cell line and expression of collagenase inhibitor. Proc. Nat. Acad. Sci. USA 1985; 82 : 5380–5384.

Wooley D. E., Roberts D. R., Evanson J. M., Small molecular weight serum protein which specifically inhibits human collagenases. Nature 1976; 261 : 325–327.

Cooper T. W., Eisen A. Z., Stricklin G. P., Welgus H. G., Platelet derived collagenase inhibitor: characterisation and subcellular localisation. Proc. Natl. Acad. Sci. USA. 1985; 82: 2771–2783.

Grobelny D., Poncz L., Galardy R. E., Inhibition of human skin fibroblast collagenase, thermolysin, and pseudomonas aeruginosa elastase by peptide hydroxamic acids. Biochem. 1992;31 : 7152–7154.

Mullins D. E. etal, Biochem. Biophys Acta (1983) 695 117–214.

Schultz G. S., Strelow S., Stern G. A., Chegini N., Grant M. B., Galardy R. E., Grobelny D., Rously J. J., Stonecipher K., Parmley V. and Khaw P. T. Treatment of Alkali-Injured Rabbit Corneas with a Synthetic Inhibitor of Matrix Metalloproteinases. Investigative Ophthalmology and Visual. Science Vol 33, No. 12 3325–3331.

Woost P. C., Jumblatt, M. M., Eiferman R. A., and Schultz G. S., Growth Factors in Corneal Endothelial Cells : I. Stimulation of Bovine Corneal Endothelial Cell DNA Synthesis by Defined Growth Factors. Cornea, 1992; 11(1) : 1–10.

Khaw P. T., Ward S., Porter A., Grierson I., Hitchings R. A., Rice N. S. C., The Long Term Effects of 5. Fluorouracil and Sodium Butyrate on Human Tenons Capsule Fibroblasts. Investigative Ophthalmology and Visual Science 1992; 33: 2043–2052.

Nagase H., Barrett A. J., Woessner J. F. Jr., Nomenclature and Glossary of Matrix Metalloproteinases. MATRIX (Suppl) 1992; 1:421–424.

Gabbiani G., Hirschel B. J., Ryan G. B., and et al. Granulation tissue as a contractile organ. A study of structure and function. J. Exp. Med. 1972; 135:719–734.

Ehrlich H. P. and Rajaratnam J. B. M. Cell locomotion forces versus cell contraction forces for collagen lattice contraction: an in vitro model of wound healing. Tiss. Cell 1990; 22: 407–417.

Schor S. L., Allen T. D. and Harrison C. J. Cell migration through three-dimensional gels of native collagen fibres: collagenolytic activity is not required for the migration of two permanent cell lines. J. Cell Sci. 1980; 46: 171–186.

Nakagawa S., Pawelek P. and Grinnell F. Long term culture of fibroblasts in contracted collagen gels: effects on cell growth and biosynthetic activity. Journal of Investigative Dermatology 1989; 93: 792–798.

Maunch C., Adelmann-Grill B., Hatamochi A., and Krieg T. Collagenase gene expression in fibroblasts is regulated by a three-dimensional contact with collagen. FEBS. Letts. 1989; 250(2): 301–305.

Lambert C. A. Pretranslational regulation of extracellular matrix macromolecules and collagenase expression in fibroblasts by mechanical forces. Lab. Invest. 1992; 60(4): 444–451.

Tarnuzzer R. W. and Schultz G. S. Quantitative competitive RT-PCR technique for growth factors and their receptors: applications in the study of corneal wound healing. Invest. Ophthalmol. Vis. Sci. 1994; 35:1318.

Heussen C. and Dowdle E. B. Electrophoretic analysis of plasminogen activators in polyacrylamide gels containing sodium dodecyl sulfate and copolymerized substrates. Analyt. Biochem. 1980; 102: 196–202.

Chomczynski P. and Sacchi N. Single-step method of RNA isolation by acid guanidinium thiocyanate-phenol-chloroform extraction. Analyt. Biochem. 1987; 162: 156–159.

Hunt R. C., Fox A., Pakalnis V. A., Sigel M. M., Kosnosky W., Choudhury P., and Black E. P. Cytokines cause cultured retinal pigment epithelial cells to secrete metalloproteinases and to contract collagen gels. Invest. Opthalmol. Vis. Sci. 1993; 34: 3179–3186.

Martin P. and Lewis J. Actin cables and epidermal movement in embryonic wound healing. Nature 1992; 360: 179–182.

We claim:

1. A method for treating healing tissue following thermal burn to inhibit or prevent scarring associated with contraction of such tissue, said tissue comprising an extracellular matrix component, said contraction being associated with untreated healing of said tissue, said method comprising administration, to a patient in need of such treatment, of a therapeutically effective regimen of a metalloproteinase inhibitor to said tissue such that said contraction is inhibited or prevented.

2. The method of claim 1 wherein said matrix metalloproteinase inhibitor is administered in a concentration of greater than 400 µg/mL.

3. The method of claim 1 wherein said matrix metalloproteinase inhibitor is a collagenase inhibitor.

4. The method of claim 1 wherein said matrix metalloproteinase inhibitor is capable of inhibiting a matrix metalloproteinase selected from the group consisting of matrix metalloproteinases 1, 2 and 3.

5. The method of claim 1 wherein said matrix metalloproteinase inhibitor is N-[2(R)-2-(hydroxamido-carbonylmethyl)-4-methylpentanoyl]L-tryptophan methylamide.

6. The method of claim 1 wherein said matrix metalloproteinase inhibitor is a peptide hydroxamic acid or a pharmaceutically acceptable derivative thereof.

7. The method of claim 1 wherein said matrix metalloproteinase inhibitor is a monoclonal or polyclonal antibody to a matrix metalloproteinase.

8. The method of claim 1 wherein said matrix metalloproteinase inhibitor is a collagenase inhibitor administered in combination with at least one other matrix metalloproteinase inhibitor.

9. The method of claim 1 wherein said matrix metalloproteinase inhibitor is administered in combination with a further pharmacologically active ingredient selected from the group consisting of antibiotics, antifungals, steroids, enzyme inhibitors, epidermal growth factors, fibronectin and aprotinin.

10. The method of claim 1 wherein said matrix metalloproteinase inhibitor is administered in combination with an inhibitor of a collagen-stimulating cytokine.

11. The method of claim 1 wherein said matrix metalloproteinase inhibitor is administered at a concentration at least about 0.4 µg/mL and less than 40 µg/mL.

12. A method of treating a human or other mammal to inhibit or prevent contraction of a post-thermal-burn tissue, said tissue comprising an extracellular matrix component, said contraction being associated with untreated healing of said tissue, comprising administering to said mammal an effective amount of a matrix metalloproteinase inhibitor to inhibit or prevent such contraction at a concentration greater than 400 µg/mL.

13. A method for inhibiting or preventing contraction of healing tissue following thermal burn, in which matrix metalloproteinase levels are not substantially chronically elevated, said tissue comprising an extracellular matrix component, said contraction being associated with untreated healing of said tissue, said method comprising the step of administering to said tissue over at least the period during which contraction occurs, an effective amount of a matrix metalloproteinase inhibitor such that said contraction is inhibited or prevented.

14. A method of inhibiting or preventing contraction of fibroblasts of healing tissue following thermal burn, said tissue comprising an extracellular matrix component, said contraction being associated with untreated healing of said tissue, said method comprising the step of administering during a time during wound healing when contraction occurs, an effective amount of a matrix metalloproteinase inhibitor to said tissue such that said contraction is inhibited or prevented.

* * * * *

UNITED STATES PATENT AND TRADEMARK OFFICE
CERTIFICATE OF CORRECTION

PATENT NO. : 6,379,667 B1
APPLICATION NO. : 09/368307
DATED : April 30, 2002
INVENTOR(S) : Khaw et al.

It is certified that error appears in the above-identified patent and that said Letters Patent is hereby corrected as shown below:

Title page, item (73) Assignee: Add –The Institute of Ophthalmology of Bath Street, London (GB)

Signed and Sealed this

Twenty-seventh Day of March, 2007

JON W. DUDAS
*Director of the United States Patent and Trademark Office*